(12) United States Patent
Tilson et al.

(10) Patent No.: US 10,363,396 B2
(45) Date of Patent: Jul. 30, 2019

(54) BIOLOGICAL NAVIGATION DEVICE

(71) Applicant: LOMA VISTA MEDICAL, INC., Burlingame, CA (US)

(72) Inventors: Alexander Quillin Tilson, Burlingame, CA (US); Mark Christopher Scheeff, San Francisco, CA (US)

(73) Assignee: LOMA VISTA MEDICAL, INC., Tempe, AZ (US)

( * ) Notice: Subject to any disclaimer, the term of this patent is extended or adjusted under 35 U.S.C. 154(b) by 153 days.

(21) Appl. No.: 15/220,065

(22) Filed: Jul. 26, 2016

(65) Prior Publication Data

US 2016/0331931 A1 Nov. 17, 2016

Related U.S. Application Data

(63) Continuation of application No. 12/912,079, filed on Oct. 26, 2010, now abandoned, which is a continuation of application No. PCT/US2009/004163, filed on Apr. 24, 2009.

(60) Provisional application No. 61/125,720, filed on Apr. 27, 2008.

(51) Int. Cl.
| | |
|---|---|
| *A61B 1/00* | (2006.01) |
| *A61M 25/01* | (2006.01) |
| *A61B 1/005* | (2006.01) |
| *A61B 1/01* | (2006.01) |
| *A61M 25/04* | (2006.01) |
| *A61M 25/10* | (2013.01) |

(52) U.S. Cl.
CPC ....... *A61M 25/0116* (2013.01); *A61B 1/0014* (2013.01); *A61B 1/0051* (2013.01); *A61B 1/00082* (2013.01); *A61B 1/00135* (2013.01); *A61B 1/00151* (2013.01); *A61B 1/00156* (2013.01); *A61B 1/01* (2013.01); *A61M 25/04* (2013.01); *A61M 25/10* (2013.01)

(58) Field of Classification Search
CPC ............ A61B 1/00156; A61B 1/00082; A61B 1/00135; A61B 1/0014; A61B 1/0051; A61B 1/01; A61B 1/00151; A61M 25/0116; A61M 25/04; A61M 25/10
See application file for complete search history.

(56) References Cited

U.S. PATENT DOCUMENTS

| | | | | |
|---|---|---|---|---|
| 4,176,662 A | * | 12/1979 | Frazer | A61B 1/00156 138/103 |
| 2004/0102681 A1 | * | 5/2004 | Gross | A61B 1/00082 600/116 |
| 2010/0240955 A1 | * | 9/2010 | Sinai | A61B 1/00082 600/116 |

* cited by examiner

*Primary Examiner* — Timothy J Neal
(74) *Attorney, Agent, or Firm* — King & Schickli, PLLC

(57) ABSTRACT

A biological navigation device that can be attached or integrated with an elongated tool, such as an endoscope, is disclosed. The device can be used for propulsive advance through a biological lumen. The device can anchor to the biological lumen. The device can subsequently or concurrently propel the endoscope and anchor the device to the biological lumen. Methods for using the same are also disclosed.

20 Claims, 17 Drawing Sheets

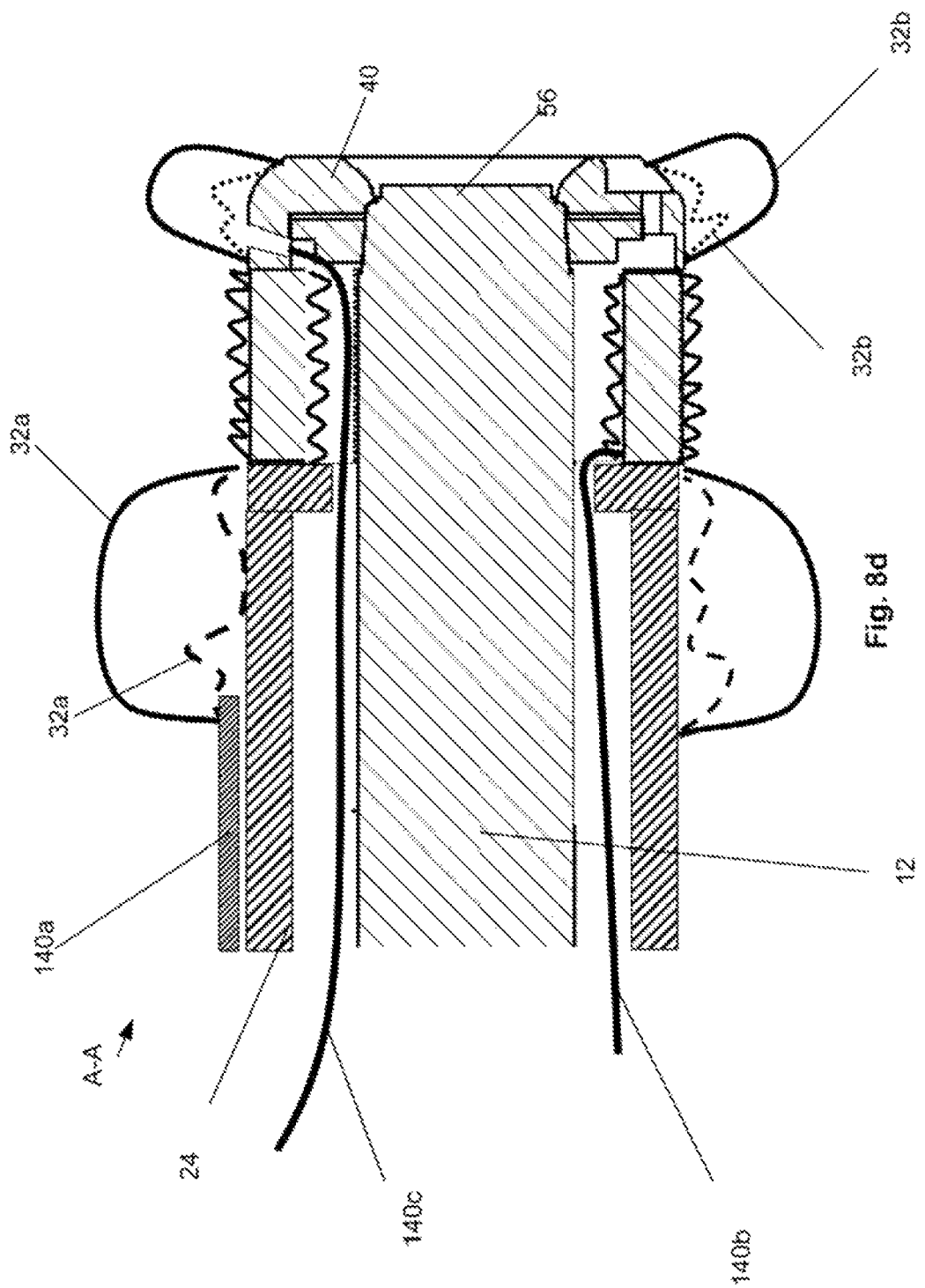

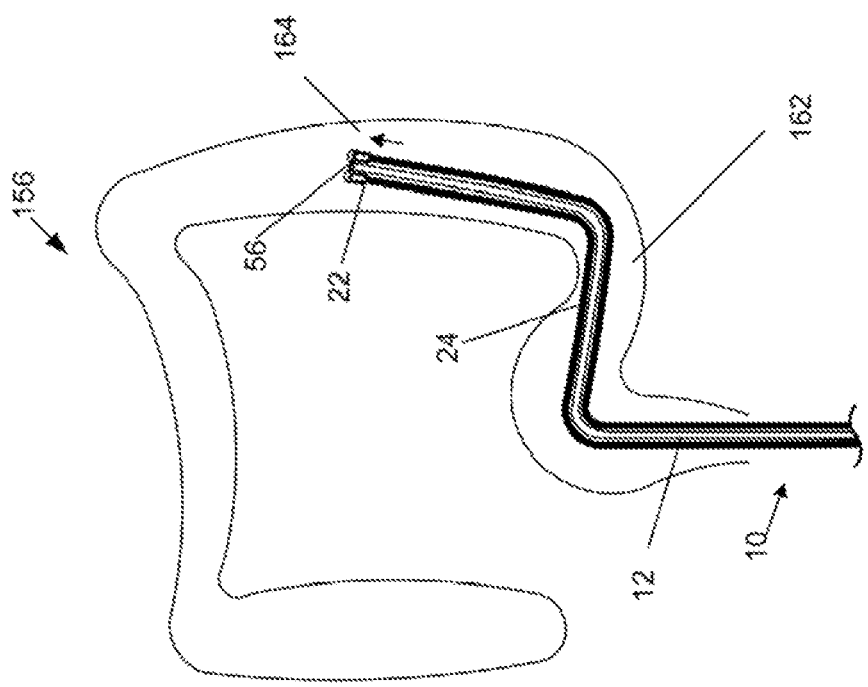

BIOLOGICAL NAVIGATION DEVICE

CROSS-REFERENCE TO REPLATED APPLICATIONS

The present application is a continuation of U.S. patent application Ser. No. 12/912,079, filed 26 Oct. 2010, which is a continuation of PCT Application No. PCT/US2009/041637, filed 24 Apr. 2009, which claims priority to U.S. Provisional Application No. 61/125,720, filed 27 Apr. 2008, each of which is incorporated herein by reference in its entirety.

BACKGROUND OF THE INVENTION

1. Field of the Invention

Devices for propelling through and exploring luminal cavities are disclosed. One such device example is an endoscope, which can be used to explore body passages. Such passages typically include, but are not limited to, the GI tract, the pulmonary and gynecological systems, urological tracts, and the coronary vasculature. Methods for use include exploration of the upper GI tract, including the small intestine and exploration of the lower part of the GI tract, for example the large intestine or colon.

2. Description of the Related Art

Colonoscopy is a diagnostic and sometimes therapeutic procedure used in the prevention, diagnosis and treatment of colon cancer, among other pathologies. With colonoscopy, polyps can be harvested before they metastasize and spread. With regular colonoscopies, the incidence of colon cancer can be substantially reduced.

The anus can provide entry into the colon for a colonoscopy. The colon extends from the rectum to the cecum and has sigmoid, descending, transverse, and ascending portions. The sigmoid colon is the s-shaped portion of the colon between the descending colon and the rectum.

Colonoscopy typically involves the anal insertion of a semi-flexible shaft. To typically navigate the colon, the forward few inches of tip are flexed or steered as the shaft is alternately pushed, pulled, and twisted in a highly skill-based attempt to advance to the end of the colon: the cecum. The medical professional imparts these motions in close proximity to the anus, where the device enters. Tip flexure has typically been accomplished by rotating wheels—one that controls cables that move the tip right-left, and one that controls cables that move the tip up-down.

Colonoscopes typically utilize various conduits or channels. The conduits or channels often contain elements that enable vision (e.g., fiber optics, CCD cameras, CMOS camera chips) and lighting (e.g., fiber optic light sources, high power LEDs (Light Emitting Diodes)), such as energy delivery and/or receipt conduits. They have conduits that provide suction or pressurization, fluid irrigation, the delivery of instruments (e.g., for cutting, coagulation, polyp removal, tissue sampling) and lens cleaning elements (typically a right angle orifice that exits near the camera, such that a fluid flush provides a cleansing wash).

Colonoscopes include articulating sections at their tip, which allow the user to position the tip. These articulating sections have rigid link bodies that rotate relative to each other through the use of pins at their connecting joints. As tensile cables pull from the periphery of the articulating sections, they impart torques, which rotate the link sections on their pins, articulating the tip section. The links are usually rotated by two or four tensile cables.

Typical commercially available colonoscopes are currently reusable. However, as disposable and other lower-cost colonoscopes are developed, these articulatable sections are no longer practical. Their high part count creates total costs that are exorbitant for a lower cost, disposable device. The pivot pins can also fall out, which can create a patient danger. Their design geometries, while suited for long life, high cost, high strength metals elements, do not readily suit themselves to the design goals of lower-cost and more readily mass-produced parts.

Suction can be utilized to remove debris or fluid. The colon can be pressurized to expand the diameter of the colon to enhance visualization.

During advancement of the colonoscope through the colon, landmarks are noted and an attempt is made to visualize a significant portion of the colon's inside wall. Therapeutic actions can occur at any time, but are typically performed during withdrawal.

Navigating the long, small diameter colonoscope shaft in compression through the colon—a circuitous route with highly irregular anatomy—can be very difficult. Studies have shown a learning curve for doctors performing colonoscopies of greater than two-hundred cases. Even with the achievement of such a practice milestone, the cecum is often not reached, thereby denying the patient the potential for a full diagnosis.

During colonoscopy, significant patient pain can result. This is typically not the result of colon wall contact or of anal entry. The primary cause of pain is thought to be stretching and gross distortion of the mesocolon (the mesentery that attaches the colon to other internal organs). This is commonly referred to as 'looping' and is a result of trying to push a long, small diameter shaft in compression as the clinician attempts to navigate a torturous colon. While attempting to advance the tip by pushing on the scope, often all that occurs is that intermediate locations are significantly stretched and grossly distorted. Due to this pain, various forms of anesthesia are typically given to the patient. Anesthesia delivery results in the direct cost of the anesthesia, the cost to professionally administer the anesthesia, the costs associated with the capital equipment and its facility layouts, and the costs associated with longer procedure time (e.g., preparation, aesthesia administration, post-procedure monitoring, and the need to have someone else drive the patient home). It has been estimated that forty percent of the cost of a colonoscopy can be attributed to the procedure's need for anesthesia.

Cleaning of colonoscopes is also an issue. Cleaning is time consuming, and lack of proper cleaning can result in disease transmission. Cleaning can utilize noxious chemicals and requires back-up scopes (some in use while others being cleaned). Cleaning also creates significant wear-and-tear of the device, which can lead to the need for more servicing.

In recent years there have been advancements in the navigation of the small intestine. One notable method is known as Double Balloon Enteroscopy. Double-balloon enteroscopy, also known as push-and-pull enteroscopy is an endoscopic technique for visualization of the small bowel. It allows for the entire gastrointestinal tract to be visualized in real time. The technique involves the use of a balloon at the end of a special enteroscope camera and an overtube, which is a tube that fits over the endoscope, and which is also fitted with a balloon. The procedure is usually done under general anesthesia, but may be done with the use of conscious sedation. The enteroscope and overtube are inserted through the mouth and passed in conventional fashion (that is, as with gastroscopy) into the small bowel. Following this, the endoscope is advanced a small distance in front of the overtube and the balloon at the end is inflated. Using the assistance of friction at the interface of the enteroscope and intestinal wall, the small bowel is accordioned back to the overtube. The overtube balloon is then deployed, and the enteroscope balloon is deflated. The process is then continued until the entire small bowel is visualized. The double-balloon enteroscope can also be passed in retrograde fashion, through the colon and into the ileum to visualize the end of the small bowel.

Though the procedure has played a vital role in the diagnosis and treatment of disease in this part of the GI tract, it remains problematic in several regards. Like colonoscopy, it suffers from looping. A long and flexible shaft is pushed, but instead of the tip moving forward, it often merely moves inadvertently in intermediate locations. The procedure requires significant skill, is laborious and time consuming—usually taking more than an hour.

In both colonoscopy and in navigation of the small intestine, it would be advantageous to have a device that enabled local 'pull' motion, i.e., if the device could pull itself forward locally, rather than having to be pushed at a far proximal and less effective location.

Methods have been suggested which create a force reaction location outside of the body. Others have been suggested which create a force reaction location—necessary to advance the endoscope—within the body, including local to the endoscope tip. Internal devices typically operate proximal to the tip's articulating section, which can be kinematically disadvantageous relative to being located distal to the articulating section.

Endoscopic devices have found it notably challenging to create methods to appropriately navigate through torturous geometries, particularly without undue colon wall stresses and subsequent mesocolon stretch. Steering kinematics are critical and have been an ongoing challenge—certainly for existing colonoscopes (which result in 'looping'), but also to more effective next-generation devices.

The systems proposed to-date have geometries that create suboptimal steering efficacies. When a propulsion element is substantially distal to the tip articulating section, it can be vectored in that direction when propelled. This can be highly advantageous relative to systems in which the propulsive element is located proximal to the articulating section. In this situation, disadvantageous kinematics are created when the tip is retroflexed and is pointing in one desired direction of advance and the system advance is attempted. The system does not move in the direction of the retroflexed tip, but rather in the direction of the system proximal to that section. When the system is coaxial, these directions are the same. However, should the tip be retroflexed back 180 degrees, the desired advance direction (i.e., tip pointing direction) and actual advance direction are 180 degrees apart. The driven section presumes a vector—typically an axial manner—with the steering tip only having efficacy as it relates to its interaction with luminal walls. In endoscopy, this wall interaction is undesirable—it creates unnecessary wall stress and trauma, and can be a significant contributor to gross wall distortion, known as looping. It would therefore be desirable to have system designs that enable more lumen-centric steering that can point the articulating section in a direction and move in that pointed direction as the unit is advanced through the colon's straights and curvatures.

Such kinematic enablement could be achieved through a novel, dedicated system. Alternatively, it could be enabled through a device that worked additive to existing endoscopes. This would be advantageous, in that it would utilize a vast installed base of advanced hardware, software, and training. Such 'retrofit' devices could potentially achieve scaled utilization in an accelerated manner.

Devices to achieve these performance goals will often have challenges with optimal material selection. The desired structure can have a rare combination of requisite features: softness, strength, radial stiffness, low thickness, freedom from leaks, flex-crack resistance, puncture resistance, appropriate coefficient of friction, the potential for modifiable geometry as a function of length, and appropriate manufacturability and cost. Monolithic materials often prove insufficient at providing the variety of requisite specifications.

BRIEF SUMMARY OF THE INVENTION

A device for navigation through a biological lumen is disclosed. The device can have a propulsion device and an endoluminal tool. The actuator can have an actuator outer wall and an actuator inner wall. The propulsion device can have an extendable actuator and an anchor, wherein the actuator is distal to the anchor. The endoluminal tool can be attached to the actuator.

The actuator can have an actuator lumen extending through a distal terminal end of the actuator. The actuator lumen can be formed by the actuator inner wall. The actuator lumen can extend through the proximal and/or distal terminal ends of the actuator. The actuator lumen can extend through the entire actuator, opening at both terminal ends of the actuator.

The anchor can be radially expandable. The anchor can be inflatable. The anchor can be or have a balloon.

The endoluminal tool can have a longitudinal axis. The actuator can be extendable along the longitudinal axis. The actuator can have an expanded configuration and a retracted configuration. The outer diameter of the actuator in the expanded configuration can be substantially equal to the outer diameter of the actuator in the contracted configuration.

The actuator can be inflatable. The actuator can have one or more bellows. The bellows can have a hollow bellows lumen. The endoluminal tool can be positioned in the hollow bellows lumen.

The endoluminal tool can have or be an endoscope. The endoluminal tool can have an articulation section. The anchor can be distal to the articulating section of the endoluminal tool.

The actuator, for example the bellows, can have a fiber-reinforced laminate. The actuator can have a spring. The spring can be a helical or a leaf spring. The spring can have a circular or rectangular (e.g., a substantially flat spring) cross-section of the coil of the spring.

A device for navigation through a biological lumen is also disclosed that can have an endoluminal tool and a bladder defining an inflatable extendable volume. The bladder can be annular and define an inner lumen radially internal to, and not in fluid communication with, the inflatable extendable volume. The endoluminal tool can be located in the inner lumen. The distal end of the endoluminal tool can be mechanically coupled to the distal end of the distal end of the bladder, for example, via an attachment clamp distal to the bladder.

Also disclosed is a device for navigation through a biological lumen that can have an endoluminal tool having an articulatible section, and a bellows attached to the endoluminal tool distal to the articulatible section. The bellows can be annular. The bellows can form a bellows lumen. A length of the endoluminal tool can be located in the bellows lumen.

The bellows can longitudinally expand when inflated. The bellows can have a substantially constant outer diameter in a deflated configuration with respect to an inflated configuration. A urethane adhesive can attach a spring to the outer wall of the bellows.

Furthermore, a device for navigating through a biological lumen having a propulsion device having an actuator and an overtube, and an endoluminal tool is disclosed. The actuator can be distal to the overtube. The endoluminal tool can be attached to the actuator.

A method for navigating through a biological lumen is also disclosed. The method can include attaching a distal end of a propulsion device to a distal end of an endoluminal tool and extending the actuator. The method can include pushing the overtube. Extending the actuator can include inflating the actuator. The method can include slidably translating the overtube with respect to the endoluminal tool. The overtube can be directly or not directly attached to the endoluminal tool. The method can include clamping the propulsion device to the endoluminal tool.

A method is disclosed for navigating through a biological lumen having an inner wall including inserting a device into the biological lumen, anchoring the device to the inner wall of the biological lumen, and extending the actuator. The device can have an actuator and an anchor, and the actuator can be distal to the anchor. The device can be attached to an endoluminal tool extending proximal to the device.

Extending the actuator can include advancing the device along the biological lumen. Extending the actuator can include delivering pressurized fluid to the actuator and not exposing the endoluminal tool to the pressurized fluid.

BRIEF DESCRIPTION OF THE FIGURES

FIGS. 8a through 8d illustrate variations of cross-section A-A of FIG. 7.

DETAILED DESCRIPTION

A biological navigation device 10 for navigation of passageways is disclosed. The device 10 can be utilized for biological passageways. The device 10 can have an endoscope 12 for navigating portions of the GI tract. The scope 12 can be attached or integral with other elements to form an endoscopy system. The endoscopy system can continuously examine and/or treat the GI tract.

Figure 1:
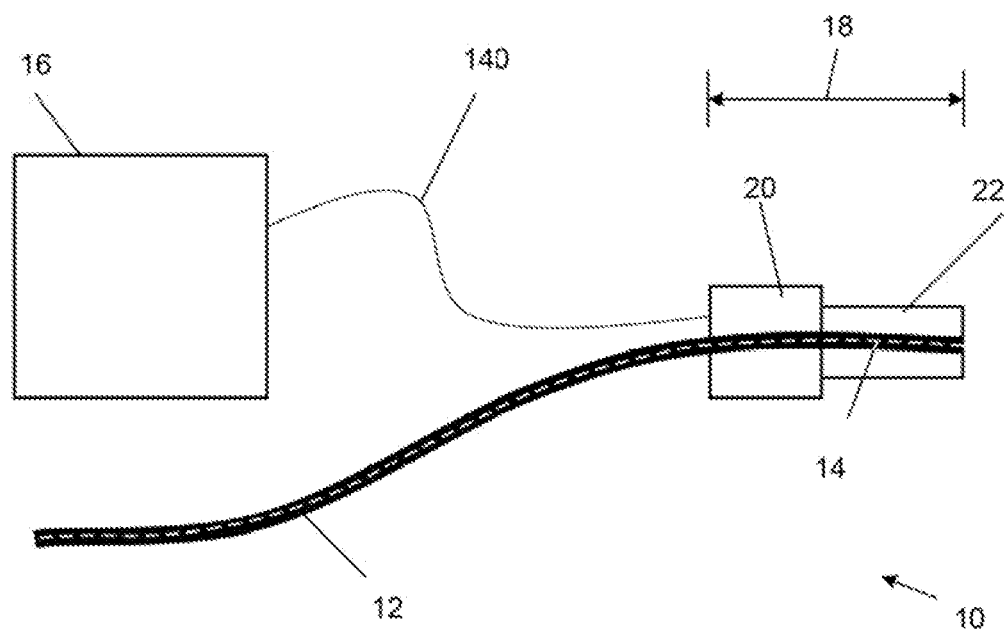
FIG. 1 is a schematic view of a variation of the device.

FIG. 1 illustrates that the device 10 can have a base 16, a propulsion tip 18, and one or more control lines 140 connecting the base 16 to the tip 18. The base 16 and tip 18 can be connected to the lines 140. The tip 18 can have an anchor 20 and an actuator 22. The anchor 20 can releasably attach to the wall of a biological lumen. The actuator 22 can controllably extend and retract in a longitudinal direction. The tip 18 may fit over an endoluminal tool for navigating the body, such as an endoscope 12. The endoluminal tool can be a device for performing therapeutic or diagnostic functions. The endoluminal tool can have a tool or endoscope longitudinal axis 14. The tip 18 can be removably or fixedly attached to the endoluminal tool.

The control lines 140 can be fluid lines (i.e., for gas and/or liquid) and/or electrical or mechanical leads, such as conductive or mechanical control wires. The control lines 140 can transmit or carry pressurized fluid (including negative pressure or vacuum), electrical signals and power, and mechanical force to the tip 18, such as to the anchor 20 and/or actuator 22.

The fluid pressure, electrical, or mechanical signals or power from the base 16 can actuate the anchor 20 and/or the actuator 22.

Figure 2:
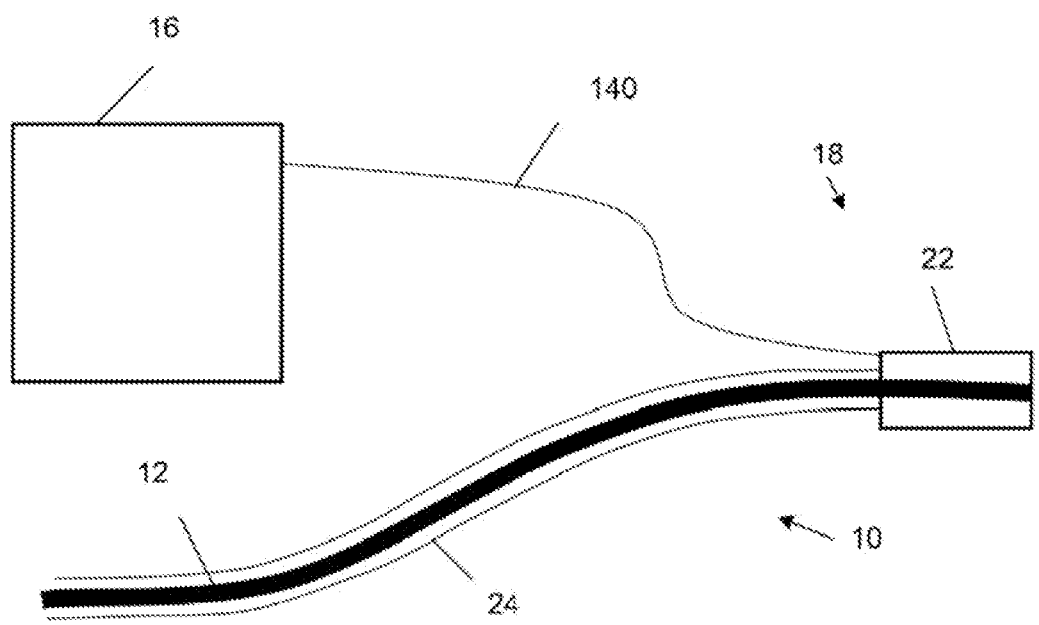
FIG. 2 is a schematic view of a variation of the device.

FIG. 2 illustrates that the device 10 can have an overtube 24. The overtube 24 may be positioned radially over the endoscope 12 or other device for navigating the body. The overtube 24 can slidably translatable with respect to the endoluminal tool. The overtube 24 can be not directly attached to the endoscope 12. The overtube can be attached to the actuator 22. The endoscope can be inside a lumen of the overtube 24. The overtube 24 may lead out of the patient's body. The overtube 24 can be sufficiently axially rigid to maintain the actuator 22 in a substantially controlled position along the length of a biological lumen during navigation of the lumen. The overtube 24 can be sufficiently flexible to navigate a tortuous biological lumen, such as a colon. All or a length of the lines 140 can embedded in or slidably or fixedly attached to the overtube 24.

The overtube 24 can be made from a polymer such as polyvinylchloride (PVC), Santoprene, Nylon, low density polyethylene (LDPE). The overtube 24 can have a durometer from about 70 shore A to about 80 shore A. The overtube 24 can have an overtube outer diameter 26 from 10 mm to 15 mm. The overtube 24 can have an overtube inner diameter 28 from about 9 mm to about 13 mm. The overtube 24 can have an overtube thickness 30 from about 0.75 mm to about 3 mm, more narrowly from about 1 mm to about 1.5 mm, for example about 1.2 mm. The overtube 24 can be a Fujinon TS-13140, TS-12140, or TS-13101 (from Fujinon Inc., Japan)

The device 10 can have no anchoring balloon 32 or can have one or more anchoring balloons 32.

Figure 3:
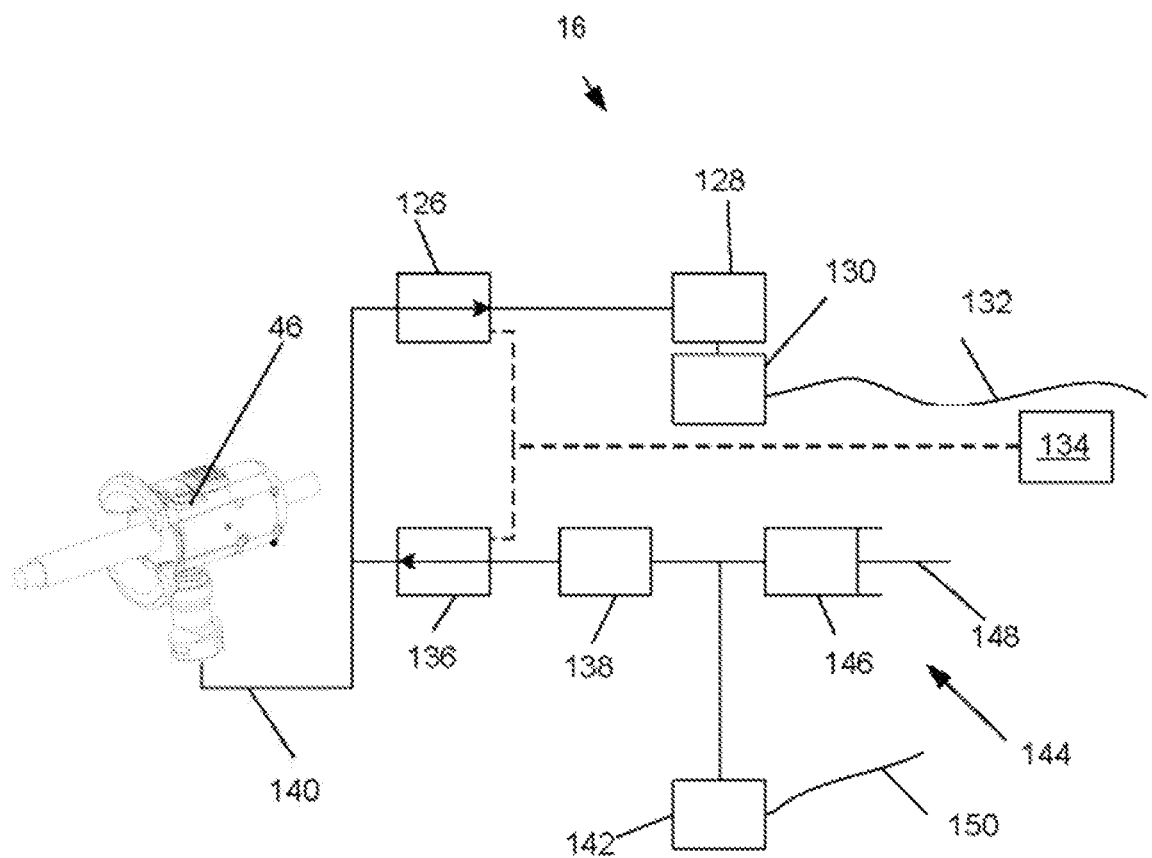
FIG. 3 is a schematic view of a variation of the base and a fluid system.

FIG. 3 shows a possible configuration for the base 16. The base 16 can have or be in fluid communication with a fluid control system 124. The base 16, for example at the base pressure port 122, can be connected to a pressure delivery line 140. The pressure delivery line 140 can be connected to an outgoing second valve 136 and/or an incoming first valve 126.

The first valve 126 can be configured to open manually and/or automatically. The first valve 126 can open when the tube pressure exceeds a maximum desired tube pressure. The first valve 126 can be connected to a vacuum pump 128. The vacuum pump 128 can be activated to deflate the tube 12 and withdraw the tube 12 or reduce the tube pressure. The vacuum pump 128 can be attached to an exhaust tank and/or directly to a bleed or drain line 132. The exhaust tank 130 can be connected to the drain line 132, for example to exhaust overflow from the exhaust tank 130.

Controls 134 can be in data communication with the first valve 126 and the second valve 136. The controls 134 can be on the base 16 (e.g., a button or switch on the base 16).

The second valve 136 can be attached to a pump 144, for example a cylinder 146 with a displacement component 148, such as a piston. A pressure regulator 138 can be in the flow path between the pump 144 and the second valve 136. The pressure regulator 138 and/or the first valve 126 can open and release pressure from the pump 144 when the tube pressure exceeds a maximum desired tube pressure.

An intake tank 142 can be fed in line (as shown) or through the pump 144 to the second valve 136, for example through the pressure regulator 138. The fluid in the intake tank 142 can be fed into the pressurized tube 12. The intake tank 142 can have a fill line 150 for filling the intake tank 142 with fluid. The fill line 150 can be fed directly to the second valve 136, pressure regulator 138 or pump 144 without the intake tank 142.

The biological navigation device 10 can have capital equipment which can provide utility to the remainder of the device 10. The capital equipment can include, for example, the elements in the fluid control system 124. The fluid control system 124 can have a fluid source (e.g., the intake tank 142 and/or fill line 150), a pressurize source such as the pump 144, a conduit for delivery of the pressurization media (e.g., the pressure delivery line 140), controls 134, system monitoring elements (e.g., can be in the controls 134). The capital equipment can reduce the profile of the tube 12, for example, in which tools can be inserted. The integrated tools can create elements that reduce waste, thereby allowing for higher value capture and less refuse.

The delivery line 140 can be attached to a handle 46 that attaches to the tip 18 or the delivery line 140 can attach directly to the tip 18.

The fluid pressurization can be controlled by a variety of user inputs, for example a button on the endoscope, handle, tip 18 or base 16, voice commands, foot pedals, or combinations thereof.

Figure 4:
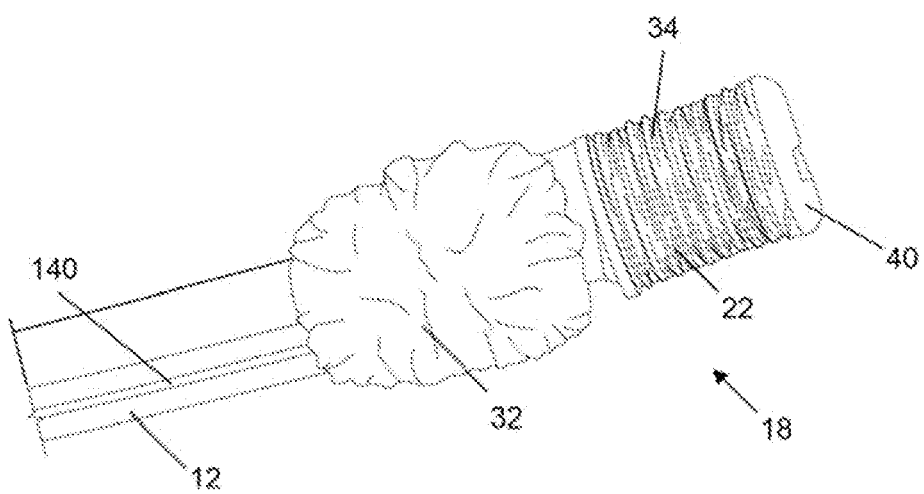
FIG. 4 illustrates a variation of the tip in a contracted or retracted configuration and a distal portion of the endoscope.
Figure 5:
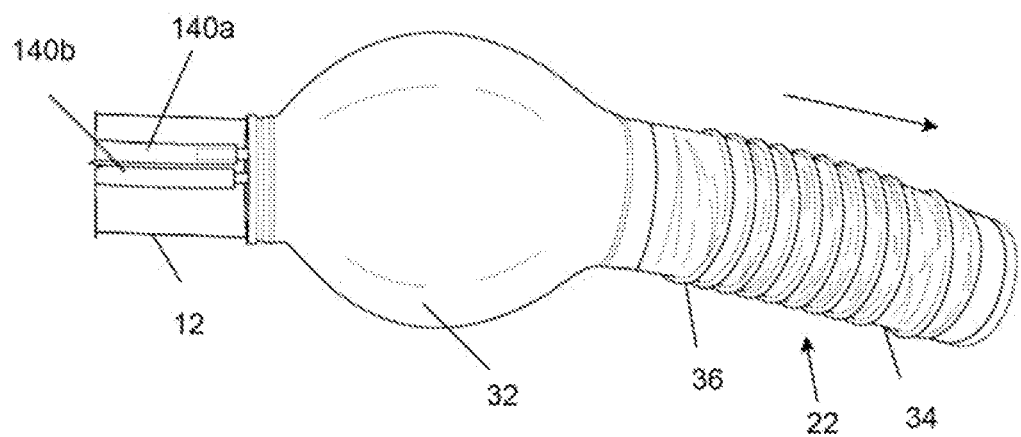
FIG. 5 illustrates a variation of the tip in a partially extended configuration and a distal portion of the endoscope.
Figure 6:
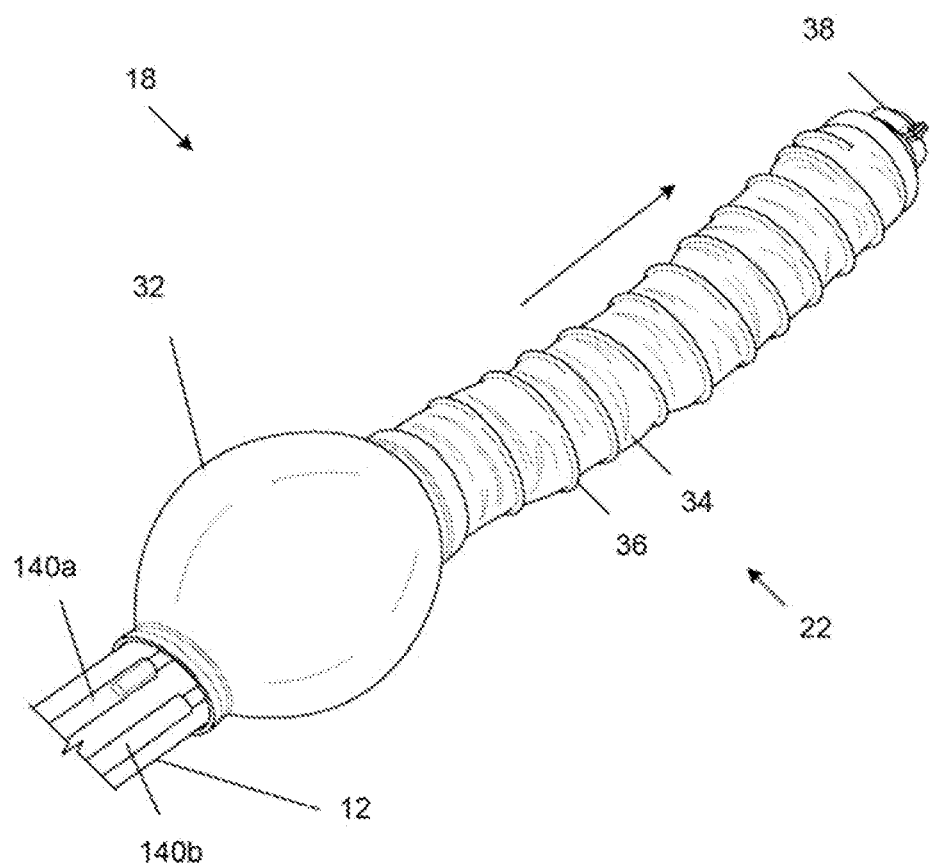
FIG. 6 illustrates a variation of the tip in an extended configuration and a distal portion of the endoscope.

FIGS. 4 through 6 illustrate that the tip 18 can have increasingly extended configurations. The anchor 20 can have one or more hooks, barbs, extendable fingers, or anchoring balloons 32. The actuator 22 can have a controllably extendable element, such as one or more springs 36. The springs 36 can be in fluid permeable or fluid impermeable bellows 34. The terminal distal end of the tip 18 can have a traumatic or atraumatic cap 40.

FIG. 4 illustrates that the anchoring balloon 32 can be partially or completely deflated and the actuator 22 retracted.

FIG. 5 illustrates that the anchoring balloon 32 can be partially or completely expanded, for example by inflating the balloon through fluid pressure delivered by a first line 140a. The device 10 can have a second line 140b. The first line 140a can transmit or carry signals, pressure, power, or combinations thereof between the base 16 and the anchor 20. The second line 140b can transmit or carry signals, pressure, power, or combinations thereof between the base 16 and the actuator 22. The actuator 22 can be in a retracted or extended configuration when the anchoring balloon 32 is expanding.

FIG. 6 illustrates that the anchoring balloon 32 can be in an expanded configuration and the actuator 22 can be extended, as shown by arrow. The actuator 22 can be activated by pressure, signals and/or power from the second line 140b.

The actuator 22 can be expanded by the delivery of pressure through second line 140b. The second line 140b can deliver a vacuum to the actuator 22 to produce a negative pressure within the fluid impermeable bellows 34 and retract the bellows 34 and the actuator 22. The bellows 34 and/or the anchoring balloon 32 can have annular or toroidal configurations.

The first line 140a can deliver positive pressure to the anchor 20 to activate or inflate the anchoring balloon 32, and negative pressure or vacuum to contract the anchoring balloon 32.

The tip 18 and endoscope can be delivered into a biological lumen, such as a colon, esophagus, or blood vessel. The anchoring balloon 32, for example in an inflated configuration, can contact the wall of the biological lumen. The balloon can exert a radial force and engage against the lumen wall, creating axial forces fixing or anchoring the anchor 20 to the lumen wall. The actuator 22 can then be expanded while the balloon remains substantially fixed against the lumen wall. The endoscope can be slidably attached to the anchor 20, but fixedly attached to the actuator 22. Hence, expansion of the actuator 22 while the balloon remains fixed against the lumen wall can advance the endoscope through the lumen, the endoscope can slide though the anchor 20 and advance concurrent with the advancement of the actuator 22.

The balloon can expand at a low pressure for example minimizing forces to the lumen wall. This expansion pressure of the balloon can be about 1 psi. The balloon can be made from a very low durometer material, for example a material that can stretch and contact the wall to a variety of anatomies at a low pressure. Latex balloons can be utilized, along with other materials, including urethanes or other elastomers.

The anchoring balloon 32 can be made from a non-elastomeric or minimally-elastomeric material. The anchoring balloon 32 can have a maximum expanded diameter larger than the diameter of the lumen wall into which the anchoring balloon 32 is to be delivered. The anchoring balloon 32 can be inflated to engage the wall without significant pressure or stretching of the anchoring balloon 32.

The actuator 22 and anchor 20 can be activated by pressure and/or vacuum from the base 16. The base 16 can be a pressure and a vacuum source. The base 16 can deliver a first pressure of about 30 psi to the actuator 22 and/or anchor 20. The base 16 can deliver a second pressure, for example less than about 5 psi, for example about 1 psi or about 2 psi, to the actuator 22 and/or anchor 20 concurrent or subsequent to the delivery of the first pressure. The base 16 can be a stand alone unit, or part of the facility (e.g., hospital or health care office) pressure and vacuum sources.

These pressures and vacuum sources can be activated by user controls. User controls can be audible, foot-activated, or manually activated. One user control can inflate the anchoring balloon 32. A second user control can expand (e.g., inflate) the actuator 22 may be inflated to drive the unit forward. The anchor 20 can be retracted by application of a vacuum from the base 16. The anchor 20 can be retracted before the bellows pressure is reduced, or the actuator 22 is otherwise retracted.

The anchoring inflation, actuator extension, anchoring deflation, and actuator retraction sequence can be repeated in sequence to advance the endoscope through a lumen. Sequential steps of inflation and contraction can be automated. For instance, pressing a single button may trigger repeated performance of the inflation, extension, deflation, retraction sequence to advance the endoscope.

Figure 7:
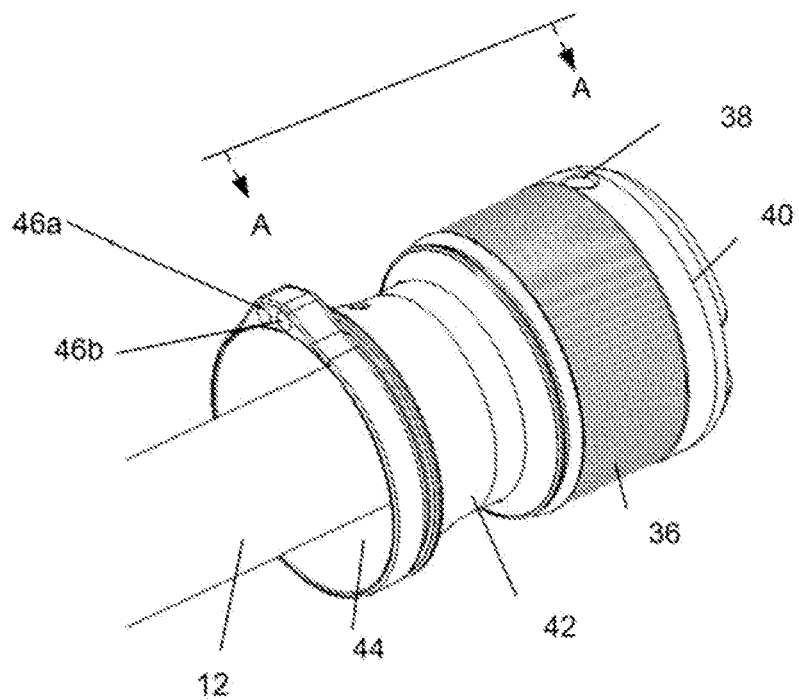
FIG. 7 illustrates a variation of the tip in a contracted configuration and a distal portion of the endoscope.

FIG. 7 illustrates that the tip 18 can have an atraumatic cap 40 and the distal terminal end of the tip 18. (The anchoring balloon 32 and the outer wall of the actuator 22 are not shown for illustrative purposes). The tip 18 can have a rigid anchor support 42. The anchor support 42 can support an anchor balloon 32. The anchor support 42 may have a conical proximal entry, such as the entry funnel 44. The entry funnel 44 may allow the proximal length of the endoscope exiting the entry funnel 44 to articulate more freely within and adjacent to the entry funnel 44. The actuator 22 can have one or more springs.

The anchor support 42 can have first and second line connectors 46*a* and 46*b*. The first and second line connectors 46*a* and 46*b* can connect to first and second lines 140*a* and 140*b*, respectively. The first and second line connectors 46 and 46*b* can deliver fluid pressure, signals and/or power between the lines 140 and the anchor 20 and actuator 22.

Figure 8A:
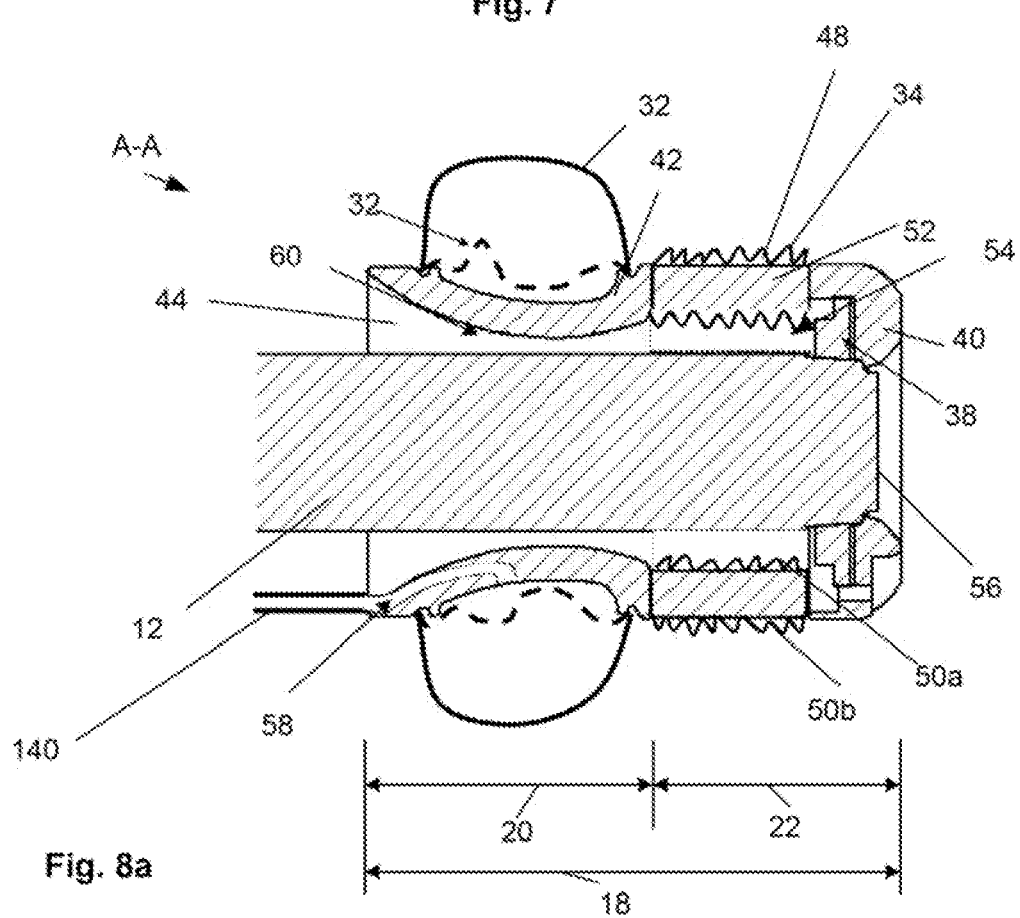

FIG. 8*a* illustrates that the anchoring balloon 32 can have inflated and collapsed (shown in phantom lines) configurations. The anchoring balloon 32 may be mounted on the anchor support 42. The anchor support 42 may encircle the endoscope in a support lumen 60. The anchor support 42 can block the anchor balloon 32 from clamping to the endoscope or from exposure to the pressure in the inflated anchor balloon 32. The anchor support 42 can have a balloon port 58 connecting flow to or from the line 140 from the line connector to the anchoring balloon 32 or actuator 22.

The actuator 22 can have an actuating body 52. The actuating body 52 can be expandable. The actuating body 52 can resilient or deformable. The actuating body 52 can have one or more springs, foam, sponge, elastomeric tube, fluid-filled and/or gel-filled annular bladder, magnets, or combinations thereof. The device 10 can have no actuating body 52.

The actuator 22 can have an inner wall 50*a* and/or an outer wall 50*b*. The inner and/or outer walls 50 can be fluid impermeable. A fluid tight, or fluid-sealed, actuator chamber 48 or volume can be between the outer wall 50*b* and the inner wall 50*a*. The outer walls 50*b* of the actuator chamber 48 can form pleated bellows 34. The bellows 34 can be an inflatable bladder. The bellows 34 can form an annular shape. The bellows 34 can form a bellows lumen 54 through which the endoscope can be placed. The endoscope can be isolated from exposure to the pressure in the bellows 34. The bellows 34 can controllably expand along the direction of the endoscopic longitudinal axis. The inner and/or outer diameter of the bellows 34 in an expanded (e.g., inflated) configuration can be substantially equal to the inner and/or outer diameter, respectively, of the bellows 34 in a retracted (e.g., deflated) configuration. The anchor support 42 can have an actuator port 70 connecting the second line connector 46*b* to the actuator chamber 48.

The inner wall 50*a* and/or outer wall 50*b* can be attached at points or along the entire length of the actuating body 52. For example, the inner wall 50*a* can be attached to the inner diameter of the actuator body 52 and the outer wall 50*b* can be attached to the outer diameter of the actuator body 52.

The anchor support 42 and/or the bellows 34 can have an annular shape. The endoscope may pass thru the inner lumen of the anchor support 42 and the bellows 34.

The tip 18 may be placed distal to an articulating section on the endoscope. The tip 18 can be directionally oriented by the endoscope. The tip 18 can be partially or completely overlapping in length with the articulate section of the endoscope.

The tip 18 can have a releasable attachment clamp 38. The attachment clamp 38 can be clamped onto the distal end of the endoscope. The clamp can removably attach the actuator to the endoscope. The attachment clamp 38 can interface with shear geometry in the endoscope. As the clamp engages this shear groove in the scope, the clamp can couple, forward and reverse motion of the bellows 34 to forward and reverse motion of the endoscope. The clamp can be a collet and/or split clamp and/or a snap ring. The clamp can be made to interface with the endoscope without any endoscope modification required.

The distal end of the endoscope can have an endoscope face. The endoscope face can have exposed therapeutic and diagnostic instruments. The endoscope face can be exposed through a port in the cap 40 at the distal end of the tip 18.

Figure 8B:
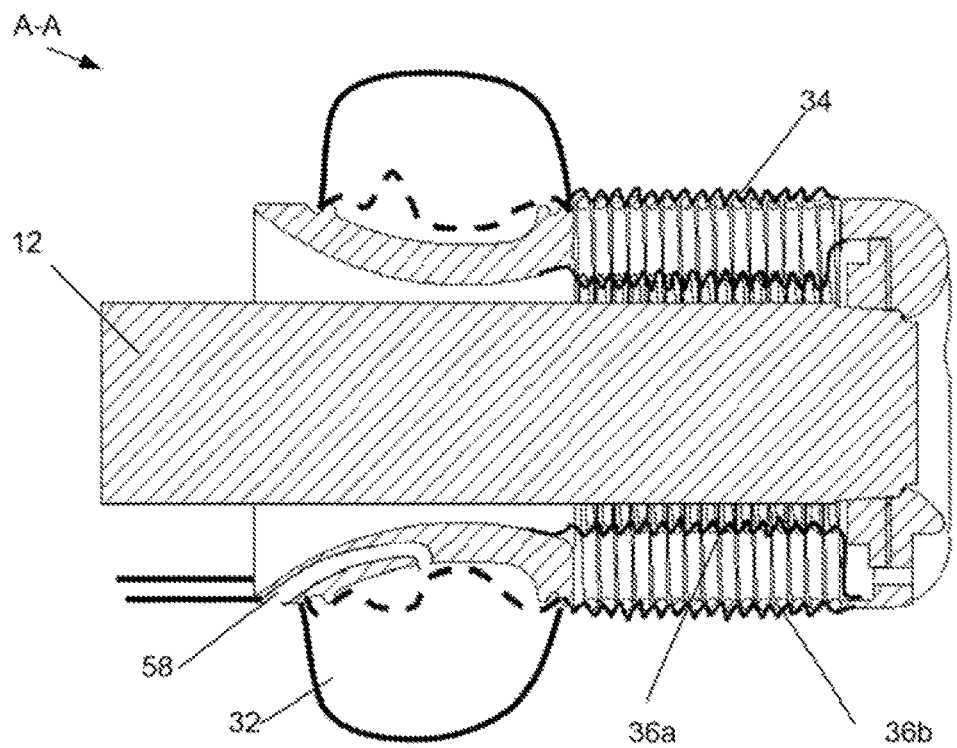

FIG. 8*b* illustrates that the actuator body 52 can be one or more springs 36. The actuator body 52 can have an inner spring 36*a* and an outer spring 36*b*. The outer diameter of the outer spring 36*b* can be attached to the outer wall 50*b* of the bellows 34. The inner diameter of the inner spring 36*a* can be attached to the inner wall 50*a* of the bellows 34.

Figure 8C:
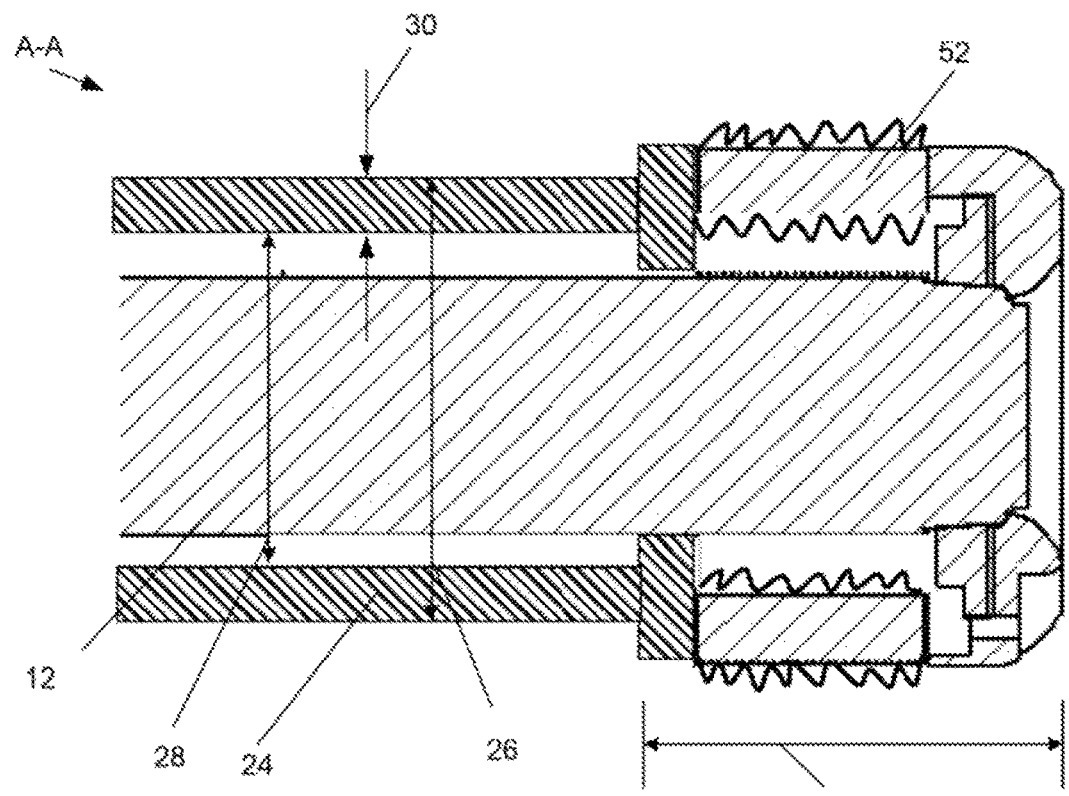

The anchoring balloon 32 may be replaced or augmented by an overtube 24. FIG. 8*c* illustrates that the anchoring balloon 32 has been replaced by an overtube 24. The overtube 24 may be a tube that encloses or partially encloses the endoscope 12. The overtube 24 may lead out of the body such that the physician can manipulate the tube. The overtube 24 may be sufficiently rigid to provide a reaction force to the actuator. The overtube 24 may be sufficiently flexible to be navigated thru the body.

FIG. 8*d* illustrates that the device 10 can have a proximal anchoring balloon 32*a* and a distal anchoring balloon 32*b* (shown in an inflated configuration in solid lines and a deflated configuration in phantom lines). The distal balloon 32*b* can be attached to the cap 40. The distal balloon 32*b* can be in fluid communication with a third line 140*c* through the cap 40.

The lines 140 can attach to the anchoring balloons 32 and actuator chamber 48 through a connector and balloon port 58 as shown elsewhere herein. The first line 140*a* can connect directly to the proximal balloon 32*a* and/or to the proximal balloon 32*a* via a direct connector into the proximal balloon 32*a*. The third line 140*c* can connect the base 16 to the distal balloon 32*b*. The third line 140*c* can connect directly to the distal balloon 32*b* and/or to the distal balloon 32*b* via a direct connector into the distal balloon 32*b*. The second line 140*b* can connect directly to the actuator 22 and/or to the actuator 22 via a direct connector into the actuator chamber 48. The lines 140 can be on the radial outside or radial inside of the support and the bellows 34.

The distal and proximal anchoring balloons 32*a* and 32*b* can be activated sequentially, concurrently, overlapping in time, or combinations thereof. For example, the device 10 can be used by performing the following, in the sequential order listed or another order: inflate the proximal anchoring balloon 32*a* anchoring the proximal balloon to the biological lumen; extend the actuator distally pulling the endoscope 12 distally with the distal end of the actuator (e.g., inflate the bellows 34); inflate the distal anchoring balloon 32*b* anchoring the distal anchoring balloon 32b to the biological lumen; deflate the proximal anchoring balloon 32a, retract the actuator pulling the proximal anchoring balloon 32a distally with the proximal end of the actuator (e.g., deflate the bellows 34); inflate the proximal anchoring balloon 32a prior to, concurrent with or subsequent to deflating the distal balloon 32b. When the anchoring balloons 32 are inflated, the anchoring balloons 32 can anchor to the wall of the biological lumen. When the anchoring balloons 32 are deflated, the anchoring balloons 32 can release the anchoring to the wall of the biological lumen.

Figure 10:
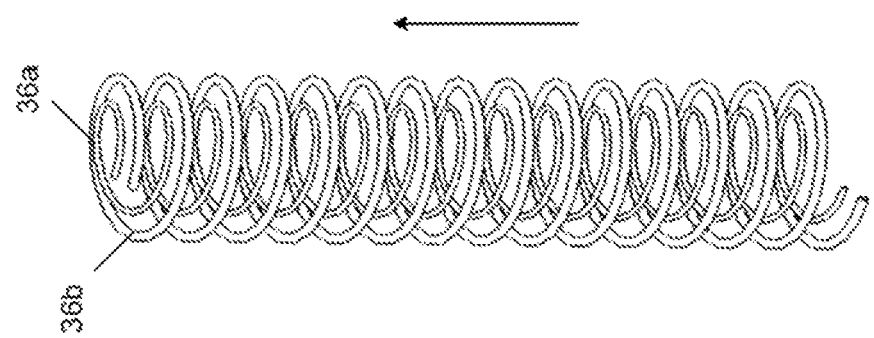
FIGS. 9 and 10 illustrate a variation of the springs of the tip of FIG. 8b in contracted and expanded configurations, respectively.

FIG. 10 shows the inner spring 36a can nest within the outer spring 36b. The springs 36 are shown retracted and extended. The bellows wall is typically coupled to the springs 36. The springs 36 provide a retraction or expansion force, in addition to the force provided by the vacuum or positive pressure. By coupling the bellows wall to the springs 36, the bellows 34 expansion and contraction can be more controlled. The springs 36 can be connected to the bellows 34 through sewing, pocketing, adhesion bonding, or combinations thereof.

Figure 9:
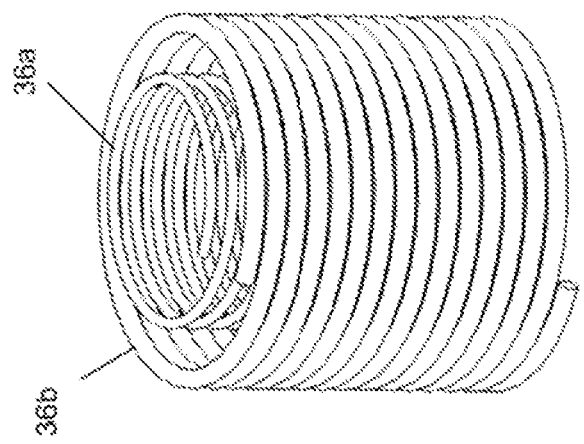

FIGS. 9 and 10 illustrate that the outer and inner spring 36a of the actuator can be configured to resiliently expand (as shown by arrow) or contract in a relaxed state. The pressure applied to the bellows 34 to activate the actuator can oppose the springs 36 to account for the desired action. For example, if the springs 36 are contracted in a relaxed state, the bellows 34 can be inflated to expand the actuator. The pressure in the bellows 34 can be released and the springs 36 can retract the bellows 34 with or without negative pressure. Also for example, if the springs 36 are expanded in a relaxed state, the bellows 34 can be deflated to contract the actuator. The pressure in the bellows 34 can be released and the springs 36 can expand the bellows 34 with or without positive pressure.

The bellows 34 may provide rapid, high-force actuation via hydraulics and/or pneumatics. The bellows 34 can be annular to allow the tool or endoscope 12 to pass through their interior. This can be done with a single bellows 34, or with an array of smaller (each individually non-annular) bellows 34. The bellows 34 can have a low-profile exterior and an interior through which the endoscope 12 fits.

Figure 11B:
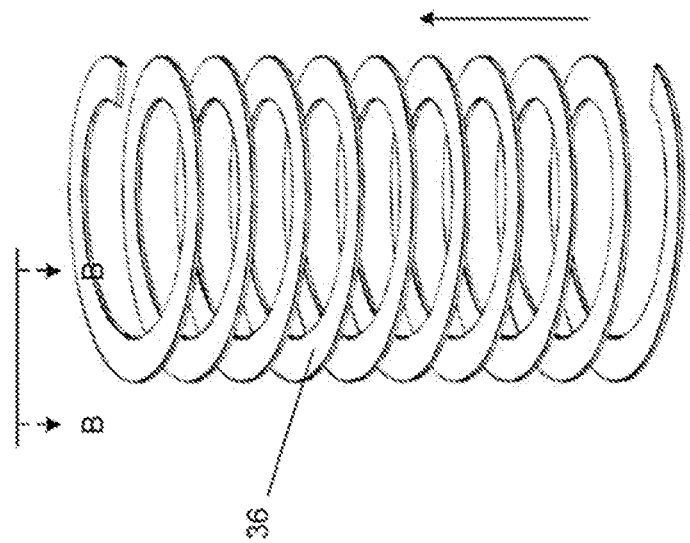
FIGS. 11a and 11b illustrate a variation of the spring of the tip of FIG. 8b in contracted and expanded configurations, respectively.
Figure 11A:
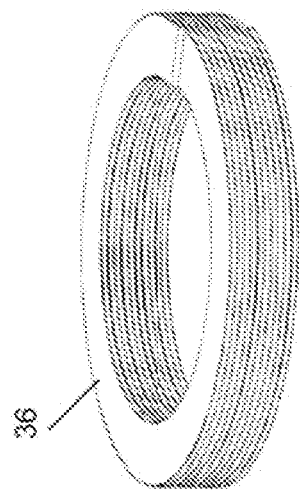

FIGS. 11a and 11b illustrate that the actuator body 52 can be one or more flat springs 36. The spring can have an outer diameter of about 0.92 in., an inner diameter of about 0.68 in., and a thickness of about 0.014 in. The spring can be made of a spring metal, for example 17-4 stainless steel. The spring can be made from a plastic. The cross section of the coil of the spring can be rectangular.

Figure 12:
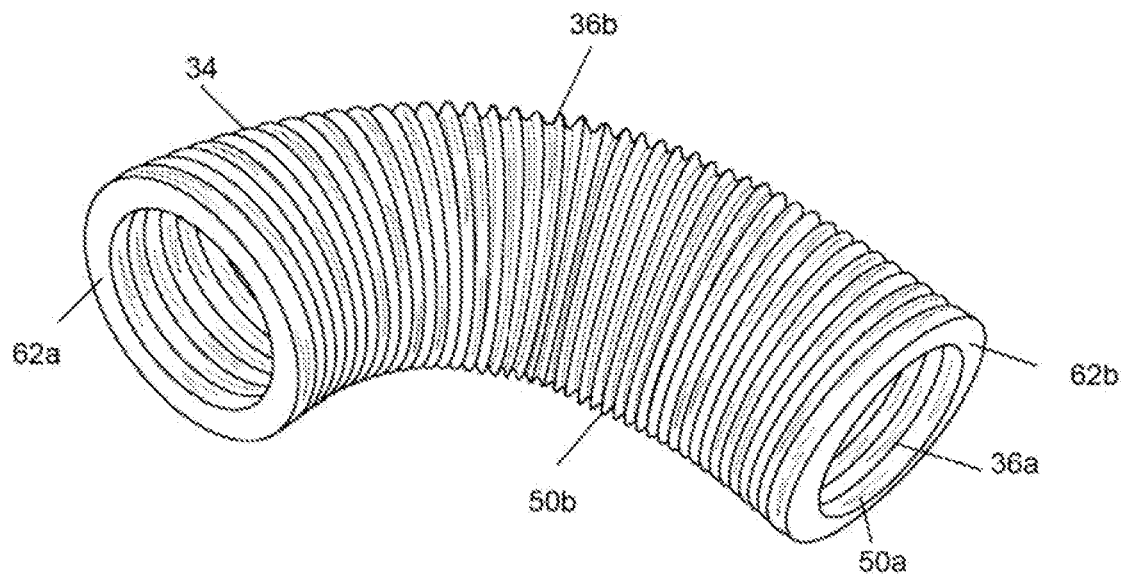
FIG. 12 illustrates a variation of the bellow.

FIG. 12 shows a bellows 34 separated from the tip 18. The bellows 34 may have a large extension ratio (compressed to expanded length), preferably 1:10. The bellows 34 may have an annular shape with a clear passage through the device 10. The interior of the bellows 34 may be placed at a pressure higher than the surrounding pressure. This may cause the bellows 34 to expand in length. The interior of the bellows 34 may be placed at a pressure lower than the surrounding pressure. This may cause the bellows 34 to contract in length.

The bellows wall material can be very thin. For example, the thickness of the bellows wall material can be from about 0.001 in. to about 0.002 in. The bellows 34 can have a compression-to-extension ratio of about 10:1 (i.e., a 0.5 in. contracted bellows 34 can expand to 5 in. at full expansion). The bellow wall material can be high strength to withstand pressure. The bellows wall material can have a low bending stiffness, high tensile strength and stiffness. The bellows wall material can bond well to adhesives.

The bellows wall material can be or include a fiber-reinforced laminate, such as Cuben Fiber (from Cubic Tech Corp., Mesa, Ariz.). The bellows wall material can be a composite of a flexible, high shear strength adhesive, engineering films, and high strength, small diameter fibers. The fibers can have a unidirectional orientation. The bellows wall material can include fibers and cloths including those made from Kevlar, spectra, nylon, Dyneema, or combinations thereof. The fiber-based elements can be deployed either as laminated unidirectional material, or woven or knitted. The bellows wall material can have layers that can be sewn together, bonded by wet adhesives or by heat activated elastomers or film adhesives.

The bellows 34 can have a bellows first end 62a and a bellows second end 62b. The bellows ends 62 can be configured to fix to the adjacent elements when the device 10 is assembled. The bellows ends 62 can be reinforced. The bellows ends 62 can be attached to or integral with the inner wall 50a and the outer wall 50b to form a fluid-tight volume.

Figure 13:
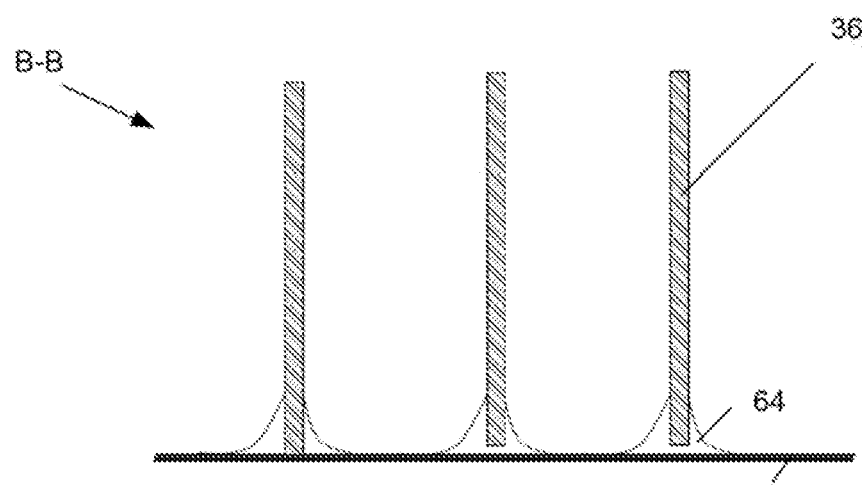
FIG. 13 is a variation of a length of cross-section B-B of FIG. 11b.

FIG. 13 illustrates that the inner or outer wall 50b of the bellows 34 can be a laminate 66. The wall can be bonded to the edge of the spring with adhesive 64. The spring can be a flat (as shown) or round spring.

The inner and/or outer wall 50b of the bellows 34 can be bonded to a thin urethane layer. The urethane layer can then be bonded to the spring, or the urethane can be pre-bonded to the spring. The urethane layer can be, for example, about 0.001 in. to about 0.002 in. thick The adhesive 64 can have low stiffness and high strength. The adhesive 64 can be heat deposited.

The adhesive 64 can be pre-deposited with the spring at a predetermined pitch. Once the adhesive 64 is melted in place at this pitch, excess adhesive 64 can be cut, leaving a predetermined amount of adhesive 64 on each of the coils, with a predetermined width and shear area. Subsequently, the inner laminate of the wall can be bonded to this surface, now with sufficient area to resist debonding from the spring, and from the laminate 66.

Figure 14:
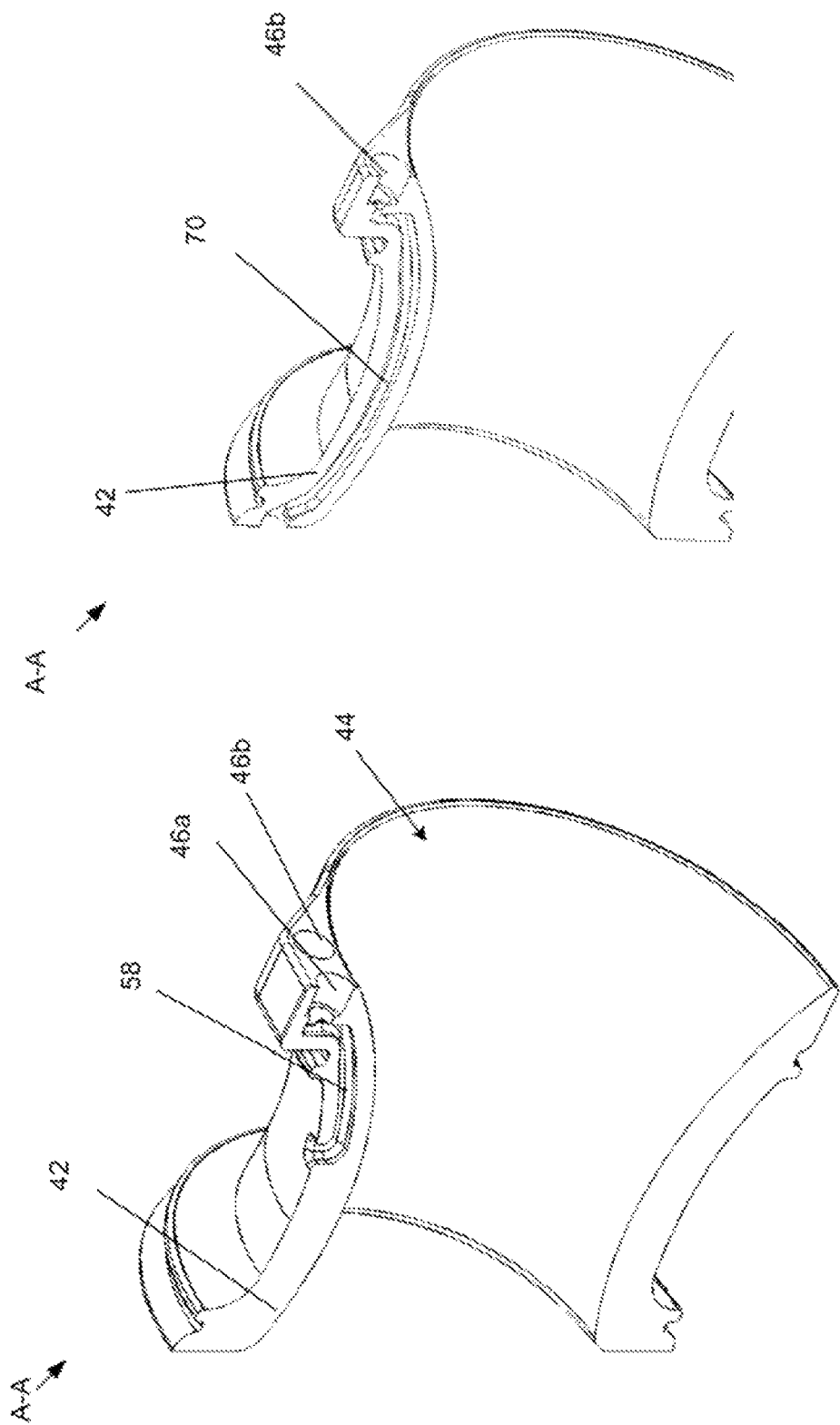
FIGS. 14a and 14b are variations of cross-section A-A of the support.

FIG. 14A illustrates that the first line 140a connector can be in fluid communication with the balloon port 58. The balloon port 58 can be in fluid communication with the anchoring balloon 32. FIG. 14B illustrates that the second line connector 46b can be in fluid communication with the actuator port 70. The actuator port 70 can be in fluid communication with the actuator chamber 48 in the bellows 34.

Figure 15:
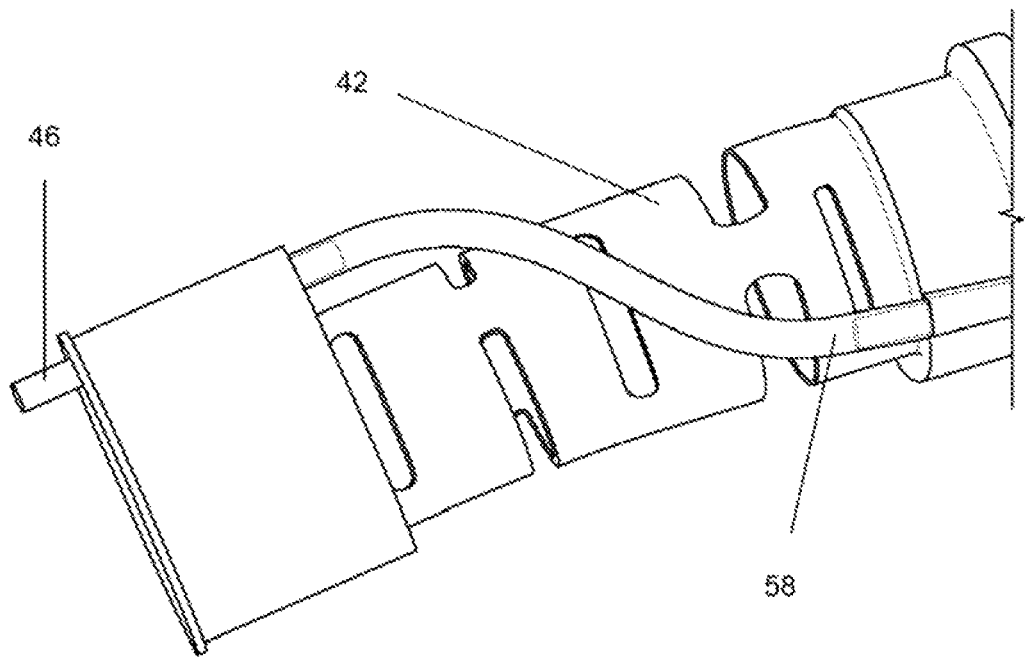
FIG. 15 illustrates a variation of the support.

FIG. 15 illustrates that the support can be flexible. The flexible support may extend over the articulating section of an endoscope 12. The flexible support may prevent the anchoring balloon 32 from clamping to the endoscope 12. The flexible support may not hinder the ability of the navigation device to steer. The flexible support may have an inflation pass-through line to connect pressure to the bellows 34 distal of the flexible support.

Figure 16:
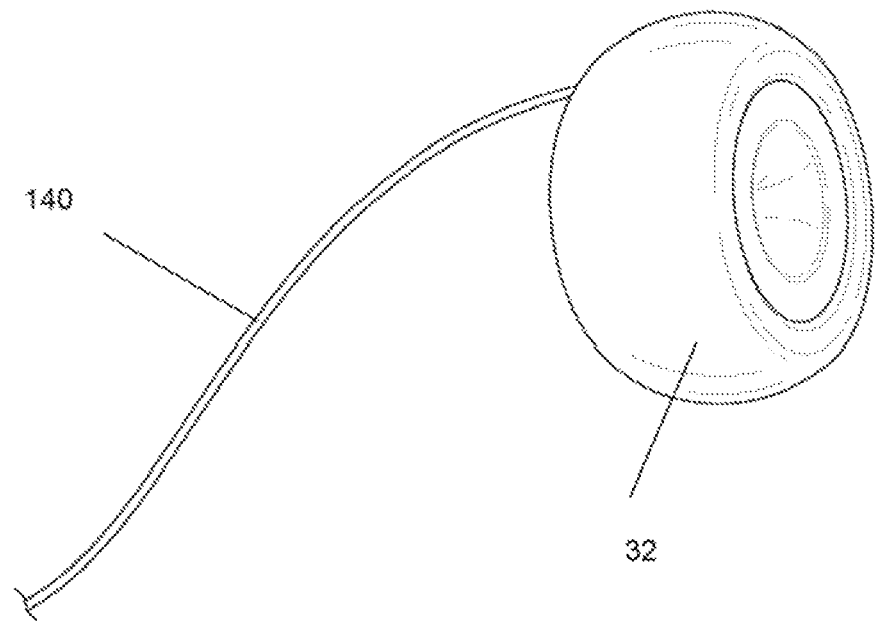
FIG. 16 illustrates a variation of the anchoring balloon.

FIG. 16 illustrates that the anchoring balloon 32 may be toroidal in shape. The anchoring balloon 32 may or may not be fluid-tight or leak-tight.

FIGS. 17a through 17f illustrate advancing the endoscope 12 through the colon using the device 10.

Figure 17B:
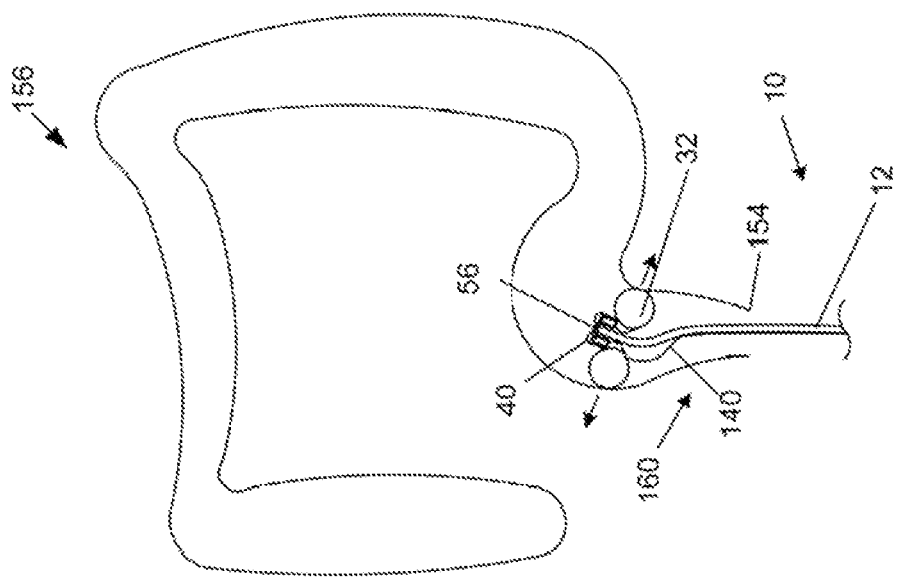
FIGS. 17a through 17g illustrate a variation of a method for using the device.
Figure 17A:
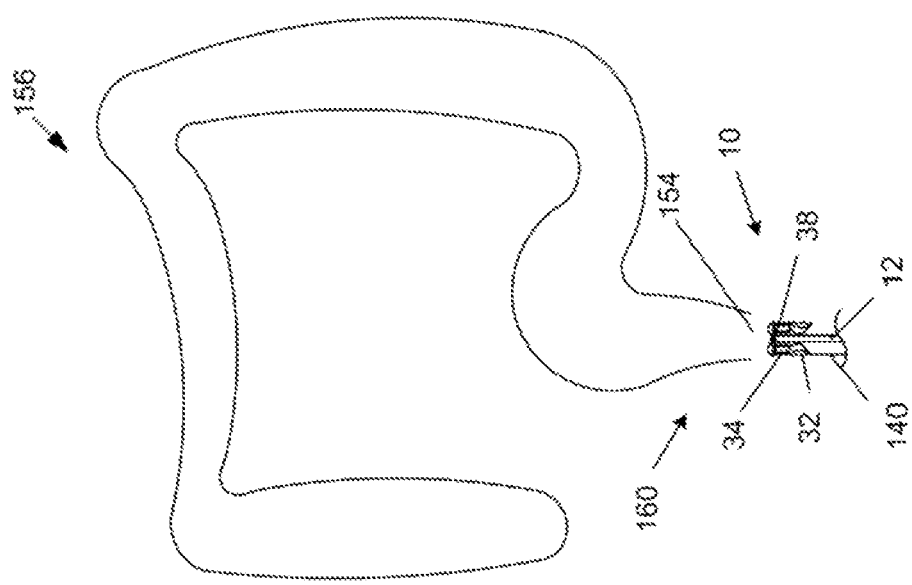

FIG. 17a illustrates that the biological navigation device 10 can be positioned before entry into the colon 156, for example via the rectum 160 after passing the anus 154. The endoscope 12 can be attached to the actuator 22 via the attachment clamp 38. For example, the endoscope 12 can be delivered by a first manufacturer and the tip 18 can be delivered by a second manufacturer, and the tip 18 can be attached to the endoscope 12 in a health care facility (e.g., hospital, doctor's office, clinic), for example by a technician or physician. The physician can use the physician's desired tip 18 with the physician's desired endoscope 12. The endoscope 12 does not need to be pre-attached to the tip 18 by the manufacturer. The physician can select the optimal tip 18 and separately select the optimal endoscope 12 shortly before the procedure based on the patient's anatomy, health issues and procedure to be performed.

FIG. 17b illustrates that the device 10 can be delivered into the rectum 160. The biological navigation device 10 can translate into the rectum 160, attached to the elongated element 28. For example, initial delivery of the device 10 into the rectum can be performed by inserting the device 10 through the anus by hand.

The biological navigation device 10 is shown having an outer diameter smaller than the inner diameter of the colon 156 for exemplary purposes. The biological navigation device 10 can have an outer diameter about equal to the inner diameter of the colon 156. For example, the tip 18 and/or endoscope 12 can substantially fill the cross-section of the length of the colon 156 occupied by the tip 18 and/or endoscope 12.

Once positioned in the colon 156, the line 140 (or first line) can deliver pressure from a base 16 to the anchoring balloon 32. The anchoring balloon 32 can expand, as shown by arrows. The anchoring balloon 32 can press against the inner wall of the colon, for example in the rectum.

The line 140 can be fixedly or slidably attached along all or part of the length of the line 140 to the endoscope 12. For example, the endoscope 12 can have collars or a channel that can slidably or fixedly attach to the line 140 as the line 140 extends distally away from the tip 18. The line 140 can be unattached to the endoscope 12 along the entire length of the line 140.

The endoscopic face 56 can be unobstructed by the cap 40. The one or more tools or other elements in the endoscopic face 56 can diagnose and treat during the delivery and advancement of the device 10 through the colon.

Figure 17D:
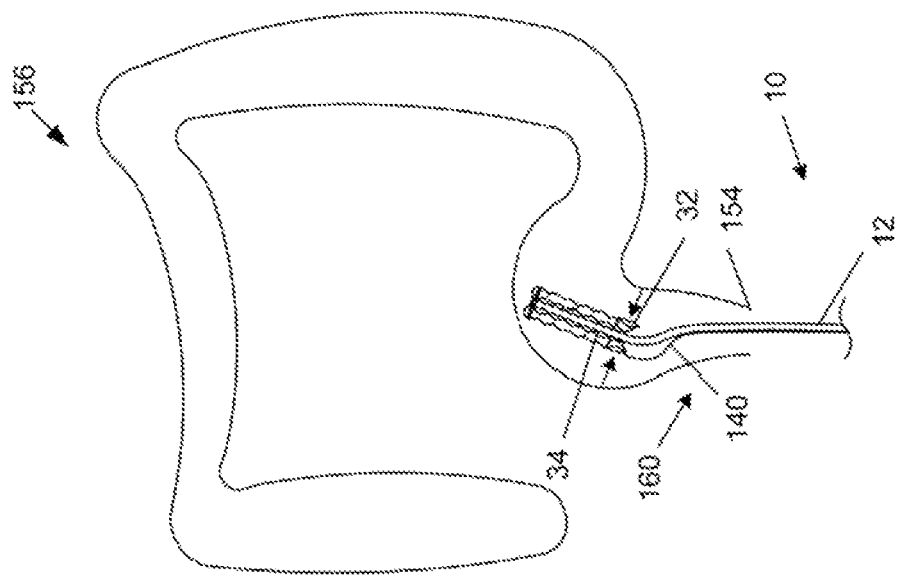
Figure 17C:
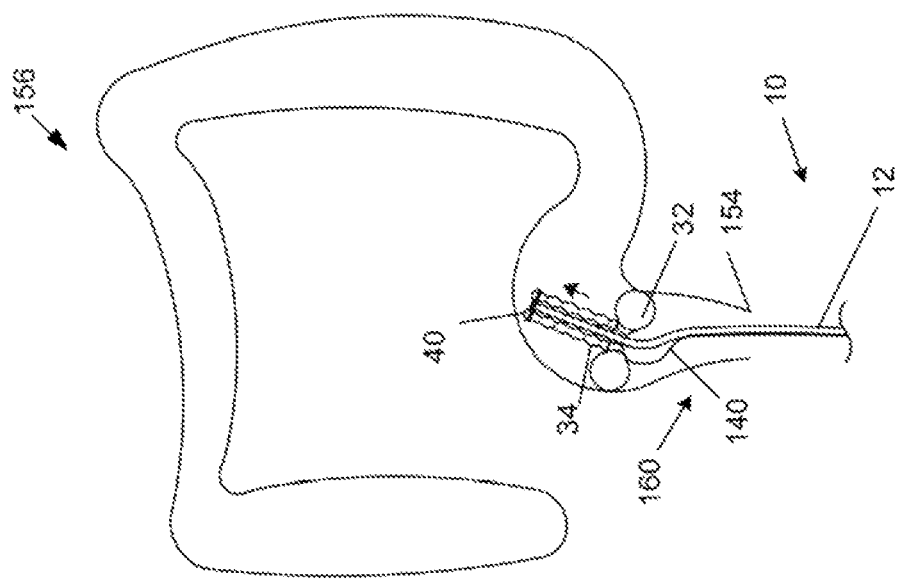

FIG. 17c illustrates that the actuator 22 can extend, as shown by arrow. For example, the line 140 (or second line) can deliver pressurized fluid from the base 16 to the bellows 34. The inflated anchoring balloon 32 can induce a resistive force against the wall of the biological lumen to keep the anchoring balloon 32 substantially stationary while the actuator 22 advances. The actuator 22 can be attached to the distal end of the endoscope 12. When the actuator 22 advances, the endoscope 12 can advance. The line 140 can remain substantially stationary. The line 140 can slide against the side of, in a channel of, or within one or more collars on the endoscope 12 when the endoscope 12 longitudinally translates relative to the line 140.

FIG. 17d illustrates that the anchoring balloon 32 can deflate or Otherwise retract, as shown by arrows. The deflation of the anchoring balloon 32 can release the tip 18 from being anchored to the biological lumen wall.

Figure 17E:
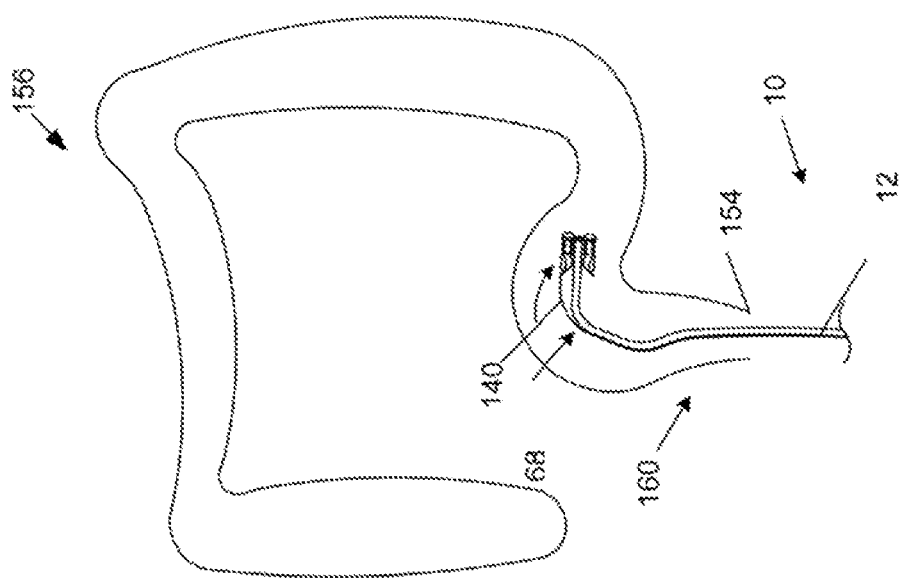

FIG. 17e illustrates that the actuator 22 can retract, as shown by arrow. For example, the bellows 34 can be deflated through the line 140 (or second line). When the actuator 22 retracts, the anchoring balloon 32 can move toward the terminal distal end of the tip 18.

Figure 17F:
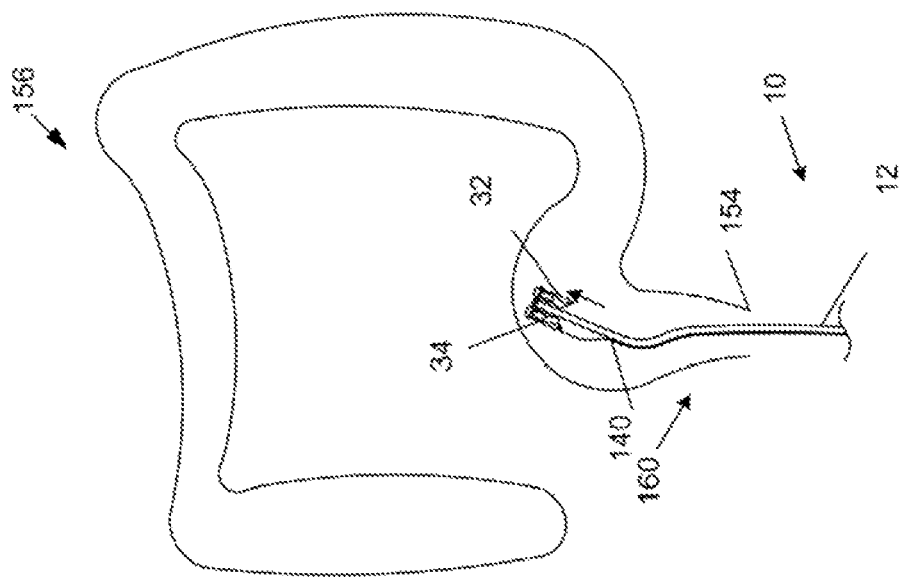

FIG. 17f illustrates that the endoscope 12 can have an articulatable section 68. The distal end of the endoscope 12 can be rotated, as shown by arrow, for example by the articulatable section 68. For example, the direction the tip 18 is pointed can be steered for the distal end of the tip 18 to follow the center of the lumen of the colon or to point the endoscopic face 56 toward the wall (e.g., to inspect or treat a polyp). At any length in the colon 156, the biological navigation device 10, such as at the endoscopic face 56, can gather diagnostic (e.g., sensing) data, such as data for visualization, tissue inductance, RF absorption or combinations thereof. At any length in the colon 156, such as at the endoscopic face 56, the biological navigation device 10 can also gather tissue samples (e.g., by performing a biopsy or removing a polyp). At any length in the colon 156, such as at the endoscopic face 56, the biological navigation device 10, can perform treatment or therapy, such as delivery of a drug onto or into tissue, tissue removal (e.g., polyp or tumor removal), or combinations thereof.

The method shown in FIGS. 17b through 17f can be repeated to steer and advance the endoscopic face 56 to a desired location.

Figure 17G:
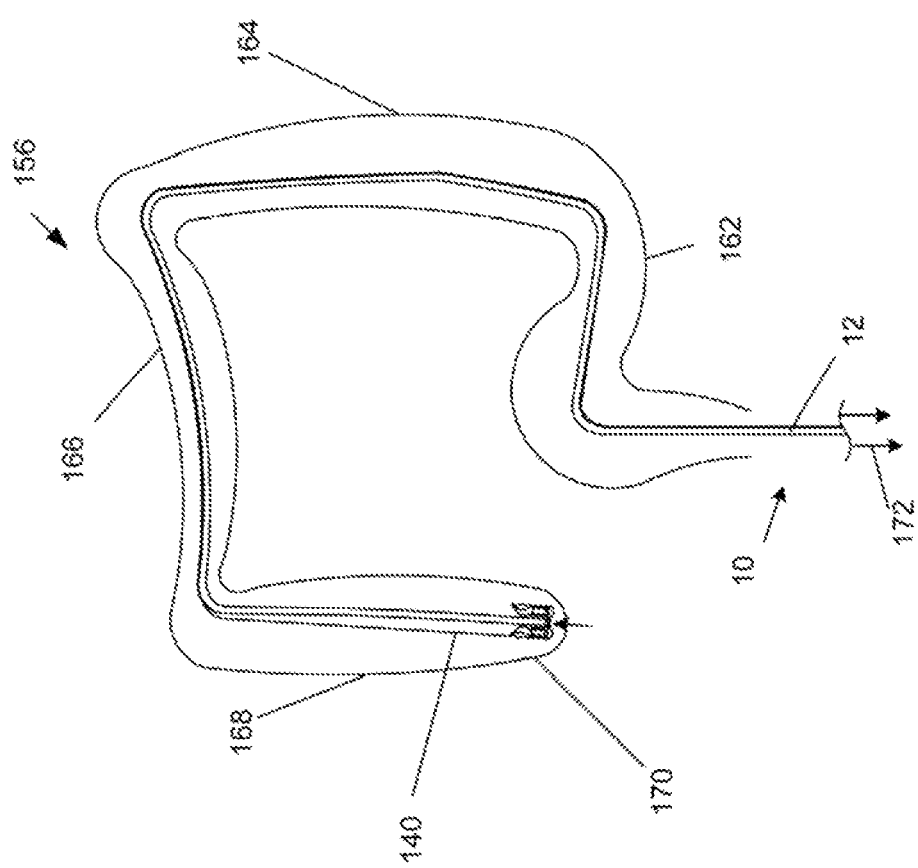

FIG. 17g illustrates that the biological navigation device 10 can be advanced along the entire colon 156, passing through the rectum 160, sigmoid colon 162, descending colon 164, transverse colon 166, ascending colon 168, and having the tip 18 in the cecum 170. The biological navigation device 10 can be withdrawn, as shown by arrows, from the colon 156, for example by applying a tensile force against the endoscope 12, as shown by arrows 172 and/or by performing the reverse of the method shown above (i.e., extend actuator 22, then inflate anchoring balloon 32, then retract actuator 22, then deflate anchoring balloon 32, then repeat as desired). The biological navigation device 10 can be withdrawn, as shown by arrows, from the colon 156, for example by applying a tensile force to the line 140.

The device 10 can deliver agents or drugs to the target site. The distal end of the device 10 can passively rotate, for example if the biological navigation device 10 (e.g., the tip 18) contacts a wall of the colon 156 (e.g., the superior wall of the rectum 160), the biological navigation device 10 can then deflect from or track to the wall of the colon 156.

Figure 18A:
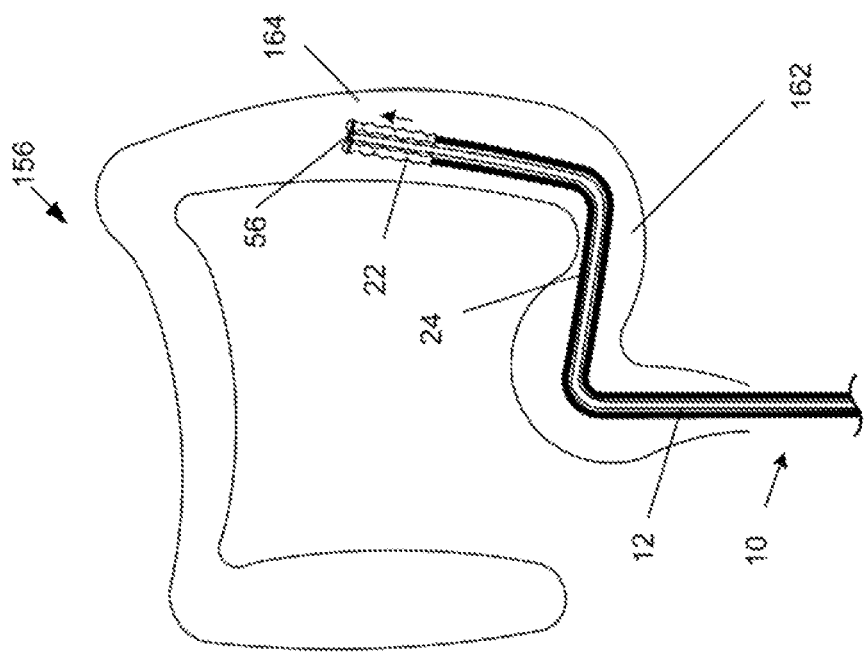
FIGS. 18a and 18c illustrate a variation of a method for using the device.

FIG. 18a illustrates that a device 10 having an overtube 24 can be deployed in a colon. The tip 18 is shown in the descending colon 164 for illustrative purposes. The line 140 (or lines) are not shown for illustrative purposes.

Figure 18B:
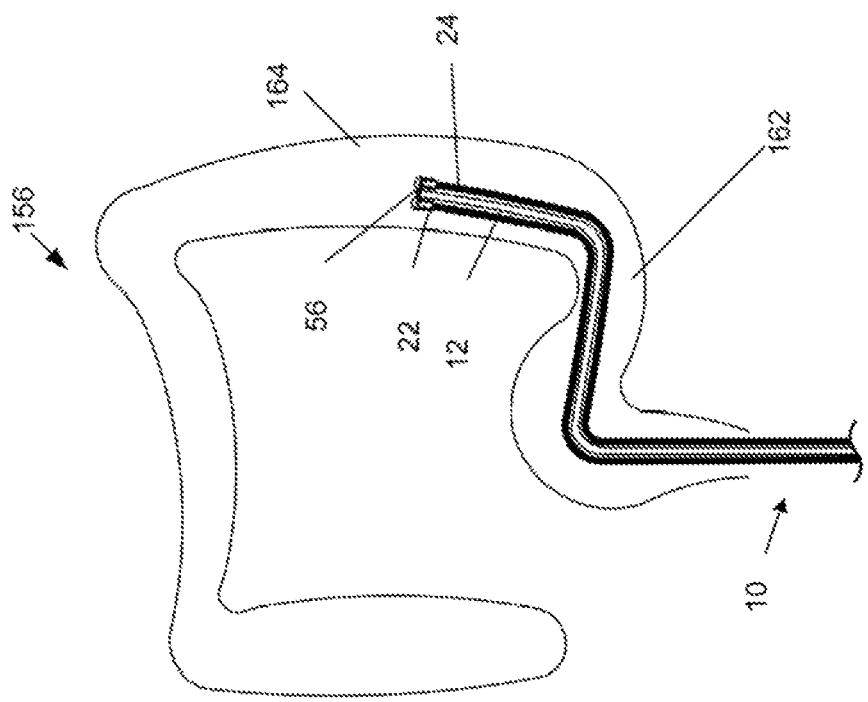

FIG. 18b illustrates that the actuator 22 can extend, as shown by arrow. The endoscope 12 can be attached to the actuator 22. The endoscope 12 can advance through the colon as the actuator 22 extends. The endoscope 12 can be slidably adjacent and within the overtube 24. A lubricant can be applied between the endoscope 12 and the overtube 24.

FIG. 18c illustrates that the actuator 22 can be retracted. The overtube 24 can slide to advance closer to the distal terminal end of the device 10. The method can be repeated to advance the endoscope 12 through the colon. The method can be reversed to withdraw the device 10 from the colon.

The endoscope 12 can be isolated from exposure to the pressure used to activate the actuator 22 and/or the anchor 20. The endoscope 12 can extend through the bellows lumen 54 and the support lumen 60.

The device 10 can be used to navigate other sections of the colon (e.g., ascending, descending, transverse, sigmoid), small intestine, esophagus, stomach, interstitial space, such as within the pleural or peritoneal membrane, blood vessels, or combinations thereof.

The biological navigation device 10 can be manually and/or actuator controlled. Control inputs can be delivered through a manually actuated controllable module, such as a joystick (e.g., for tip control) and/or a series of linear and rotary potentiometers and switches. The biological navigation device 10 can be programmed to be controlled by voice commands. The biological navigation device 10 can be controlled by a foot pedal (e.g., for tube extension or translation), and/or a combinational interface (e.g., hand controlled), for example for tip control. The user interface can be attached as part of the biological navigation device 10, and/or the user interface can be a control unit that is attached by wires to the biological navigation device 10, and/or the user interface can communicate wirelessly with the remainder of the biological navigation device 10.

The entire tip 18 can load over the distal terminal end of an endoscope 12. The tip 18 can attach to the endoscope 12, the lines 140 can be attached to the line connectors and the device 10 can be delivered into the biological lumen.

As taught herein, the device 10 can anchor locally and pull the endoscope 12 with a localized pull in the direction of the distal terminal end of the device 10 or endoscope 12 distal pointing end. The method can be repeated. Each iteration of the method can advance the endoscope 12 and the distal terminal end of the device 10, for example, from about 3 in. to about 7 in.

Any or all elements of the biological navigation device. 10 and/or other devices or apparatuses described herein can be made from, for example, a single or multiple stainless steel alloys, nickel titanium alloys (e.g., Nitinol), cobalt-chrome alloys (e.g., ELGILOY® from Elgin Specialty Metals, Elgin, Ill.; CONICHROME® from Carpenter Metals Corp., Wyomissing, Pa.), nickel-cobalt alloys (e.g., MP35N® from Magellan Industrial Trading Company, Inc., Westport, Conn.), molybdenum alloys (e.g., molybdenum TZM alloy, for example as disclosed in International Pub. No. WO 03/082363 A2, published 9 Oct. 2003, which is herein incorporated by reference in its entirety), tungsten-rhenium alloys, for example, as disclosed in International Pub. No. WO 03/082363, polymers such as polyethylene teraphathalate (PET), polyester (e.g., DACRON® from E. I. Du Pont de Nemours and Company, Wilmington, Del.), polypropylene, aromatic polyesters, such as liquid crystal polymers (e.g., Vectran, from Kuraray Co., Ltd., Tokyo, Japan), ultra high molecular weight polyethylene (i.e., extended chain, high-modulus or high-performance polyethylene) fiber and/or yarn (e.g., SPECTRA® Fiber and SPECTRA® Guard, from Honeywell International, Inc., Morris Township, NJ, or DYNEEMA® from Royal DSM N.V., Heerlen, the Netherlands), polytetrafluoroethylene (PTFE), expanded PTFE (ePTFE), polyether ketone (PEK), polyether ether ketone (PEEK), poly ether ketone ketone (PEKK) (also poly aryl ether ketone ketone), nylon, polyether-block co-polyamide polymers (e.g., PEBAX® from ATOFINA, Paris, France), aliphatic polyether polyurethanes (e.g., TECOFLEX® from Thermedics Polymer Products, Wilmington, Mass.), polyvinyl chloride (PVC), polyurethane, thermoplastic, fluorinated ethylene propylene (FEP), absorbable or resorbable polymers such as polyglycolic acid (PGA), poly-L-glycolic acid (PLGA), polylactic acid (PLA), lactic acid (PLLA), polycaprolactone (PCL), polyethyl acrylate (PEA), polydioxanone (PDS), and pseudo-polyamino tyrosine-based acids, extruded collagen, silicone, zinc, echogenic, radioactive, radiopaque materials, a biomaterial (e.g., cadaver tissue, collagen, allograft, autograft, xenograft) any of the other materials listed herein or combinations thereof. Examples of radiopaque materials are barium sulfate, zinc oxide, titanium, stainless steel, nickel-titanium alloys, tantalum and gold.

The systems, devices, elements and methods disclosed herein can be used in conjunction or substituted with any of the systems, devices, elements and methods disclosed in U.S. Pat. Nos. 5,470,632 and 5,333,568; U.S. patent application Ser. No. 12/023,986 filed 31 Jan. 2008 (now U.S. Publication No. 2008/0183038); PCT Application Nos. US 2008/052535 filed 30 Jan. 2008 (now PCT Publication No. WO 2008/095046), and US2008/052542 filed 30 Jan. 2008 (now PCT Publication No. WO 2008/095052); and U.S. Provisional Application No. 60/887,319, filed 30 Jan. 2007, 60/887,323, filed 30 Jan. 2007, and 60/949,219, filed 11 Jul. 2007, all of which are incorporated herein by reference in their entireties.

The terms colonoscope and endoscope are used for exemplary purposes and can be any deployable elongated element for use in a body lumen. Any elements described herein as singular can be pluralized (i.e., anything described as "one" can be more than one). Any species element of a genus element can have the characteristics or elements of any other species element of that genus. The above-described configurations, elements or complete assemblies and methods and their elements for carrying out the invention, and variations of aspects of the invention can be combined and modified with each other in any combination.

We claim:

1. A device for navigation through a biological lumen comprising:
   a propulsion device comprising an extendable actuator, an anchor, and an anchor support radially interior to the anchor, wherein the actuator is distal to the anchor; and
   an endoluminal tool attached to the actuator;
   wherein the anchor support is annular in shape with a conical proximal entry and fits at least partially over the endoluminal tool.

2. The device of claim 1, wherein the anchor is radially expandable.

3. The device of claim 2, wherein the anchor support blocks radially inner expansion of the anchor onto the endoluminal tool.

4. The device of claim 2, wherein the anchor support includes a first conduit in communication with the anchor and a second conduit in communication with the actuator.

5. The device of claim 1, wherein the actuator comprises a bellows.

6. The device of claim 1, wherein the actuator has an inner diameter defining an actuator lumen, and wherein the endoluminal tool is located inside the actuator lumen.

7. The device of claim 1, wherein the actuator comprises a fiber-reinforced laminate.

8. The device of claim 1, wherein the actuator includes an actuator outer wall and an actuator inner wall forming a fluid-tight chamber therebetween.

9. The device of claim 8, wherein the fluid-tight chamber is annular in shape.

10. A device for navigation through a biological lumen comprising:
    an endoluminal tool having an articulatible section;
    an annular bellows attached to a distal end of the endoluminal tool via an atraumatic cap;
    an expandable anchor; and
    an annular anchor support proximal to the bellows, said anchor support having a conical proximal entry forming a funnel adapted to receive the endoluminal tool therein.

11. The device of claim 10, wherein the funnel includes a proximal inner diameter larger than a distal inner diameter.

12. The device of claim 10, wherein the bellows comprises an outer wall comprising a fiber-reinforced laminate.

13. The device of claim 10, wherein the bellows comprises a spring.

14. A device for navigating through a biological lumen comprising:
   an extendable actuator;
   an endoluminal tool at least partially within the actuator; and
   an annular support defining an inner lumen including a conical proximal entry, wherein the endoluminal tool is within the inner lumen;
   wherein the extendable actuator connects the annular support to a distal end of the endoluminal tool.

15. The device of claim 14, wherein the actuator comprises a bellows.

16. The device of claim 14, wherein the actuator comprises a pleated inner wall and a pleated outer wall.

17. The device of claim 16, wherein the inner wall and the outer wall form an annular fluid-tight chamber therebetween.

18. The device of claim 14, further including a radially expandable balloon at least partially surrounding the annular support.

19. The device of claim 18, wherein the annular support blocks the endoluminal tool from pressure exerted by the annular balloon.

20. A device for navigating through a biological lumen comprising:
   an extendable actuator;
   an endoluminal tool at least partially within the actuator; and
   an annular support defining an inner lumen including a conical proximal entry, wherein the endoluminal tool is within the inner lumen; and
   a radially expandable balloon at least partially surrounding the annular support.

* * * * *